(12) United States Patent
Hyman

(10) Patent No.: US 7,510,856 B2
(45) Date of Patent: Mar. 31, 2009

(54) METHOD FOR PLASMID PREPARATION BY CONVERSION OF OPEN CIRCULAR PLASMID TO SUPERCOILED PLASMID

(76) Inventor: Edward D. Hyman, 4724 Hessmer Ave., Metairie, LA (US) 70002

(*) Notice: Subject to any disclaimer, the term of this patent is extended or adjusted under 35 U.S.C. 154(b) by 226 days.

(21) Appl. No.: 11/231,636

(22) Filed: Sep. 20, 2005

(65) Prior Publication Data

US 2006/0057683 A1    Mar. 16, 2006

Related U.S. Application Data

(63) Continuation-in-part of application No. 10/947,360, filed on Sep. 23, 2004, and a continuation-in-part of application No. PCT/US2004/014946, filed on May 13, 2004, and a continuation-in-part of application No. 10/837,684, filed on May 4, 2004, now abandoned, and a continuation-in-part of application No. 10/799,638, filed on Mar. 15, 2004, now abandoned.

(60) Provisional application No. 60/541,941, filed on Feb. 6, 2004, provisional application No. 60/608,923, filed on Jul. 2, 2003, provisional application No. 60/560,749, filed on Mar. 25, 2003.

(51) Int. Cl.
*C12N 15/64* (2006.01)
(52) U.S. Cl. ............... 435/91.4; 435/455; 435/468; 435/471
(58) Field of Classification Search ............... None
See application file for complete search history.

(56) References Cited

U.S. PATENT DOCUMENTS

| | | | |
|---|---|---|---|
| 5,981,735 | A | 11/1999 | Thatcher et al. |
| 6,455,287 | B1 | 9/2002 | Jem |
| 6,803,194 | B1 * | 10/2004 | Keck et al. ............ 435/6 |
| 2002/0022264 | A1 | 2/2002 | Sullivan et al. |
| 2004/0181799 | A1 | 9/2004 | Lu et al. |
| 2004/0191871 | A1 | 9/2004 | Hyman |
| 2005/0069991 | A1 | 3/2005 | Hyman |
| 2005/0084938 | A1 | 4/2005 | Hyman |

OTHER PUBLICATIONS

Arai et al., "Replication of oX174 DNA with purified enzymes", J. Biol. Chem. 256:5239-5246 (1981).
Ausubel et al., Short Protocols in Molecular Biology, 4th ed. pp. 1-22, 3-9 and 3-11 (1999).
Balasubramanian et al., "DNA strand breaking by the hydroxyl radical is governed by the accessible surface areas of the hydrogen atoms of the DNA backbone", Proc. Natl. Acad. Sci. USA 95:9738-9743 (1998).
Balke et al., "Changes in the linking of supercoiled DNA accompany growth transitions in *Escherichia coli*", J. Bacteriol. 169:4499-4506 (1987).
Beard et al., "Structural design of a eukaryotic DNA repair polymerase: DNA polymerase B", Mutation Res 460:231-244 (2000).
Best et al., "Purification of supercoiled DNA of plasmid Col E1 by RPC-5 chromatography", Anal. Biochem., 114:235-243 (1981).
Birnbiom et al., "A rapid alkaline extraction procedure for screening recombinant plasmid DNA", Nucl. Acids Res. 7:1513-1522 (1979).
Cullis et al., "Energy coupling in DNA gyrase: A thermodynamic limit to the extent of DNA supercoiling", Biochem. 31:9642-9646 (1992).
Funnell et al., "Complete enzymatic replication of plasmids containing the origin of the *Escherichia coli* chromosome", J. Biol. Chem. 261:5616-5624 (1986).
Gellert et al., "DNA gyrase: An enzyme that introduces superhelical turns into DNA", Proc. Natl. Acad. Sci USA 73:3872-3876 (1976).
Hiasa et al., "Decatenating activity of *Escherichia coli* DNA gyrase and topoisomerases I and III during oriC and pBR322 DNA replication in vitro", J. Biol. Chem. 269:2093-2099 (1994).
Hinton et al., "The synthesis of oligodeoxyribonucleotides using RNA ligase", Nucl. Acids Res., 7:453-465 (1979).
Holmes et al., "A rapid boiling method for the preparation of bacterial plasmids", Anal. Biochem. 114:193-197 (1981).
Hyman, "Preparation of plasmid DNA by sequential enzymatic digestion", BioTechniques 13:550-554 (1992).
Isfort, "Enzymatic purification of plasmid DNA", BioTechniques, 12:800-803 (1992).

(Continued)

*Primary Examiner*—James S Ketter
(74) *Attorney, Agent, or Firm*—Larson & Anderson, LLC

(57) ABSTRACT

In one embodiment of the invention, a method is provided for preparing plasmid from host cells which contain the plasmid, comprising: (a) providing a plasmid solution comprised of unligatable open circular plasmid; (b) reacting the unligatable open circular plasmid with one or more enzymes and appropriate nucleotide cofactor(s), such that unligatable open circular plasmid is converted to 3'-hydroxyl, 5'-phosphate nicked plasmid; (c) reacting the 3'-hydroxyl, 5'-phosphate nicked plasmid with a DNA ligase and DNA ligase nucleotide cofactor, such that 3'-hydroxyl, 5'-phosphate nicked plasmid is converted to relaxed covalently closed circular plasmid; and (d) reacting the relaxed covalently closed circular plasmid with a DNA gyrase and DNA gyrase nucleotide cofactor, such that relaxed covalently closed circular plasmid is converted to negatively supercoiled plasmid. In other embodiments, DNA gyrase is replaced with reverse DNA gyrase or reaction (d) is not performed.

46 Claims, No Drawings

OTHER PUBLICATIONS

Izumi et al., "Requirement for human AP endonuclease 1 for repair of 3'-blocking damage at DNA single-strand breaks induced by reactive oxygen species", Carcinogenesis 21:1329-1334 (2000).

Karimi-Busheri et al., "Repair of DNA strand gaps and nicks containing 3'phosphate and 5"-hydroxyl termini by purified mammalian enzymes", Nucl. Acids Res. 26:4395-4400 (1998).

Kim et al., "Involvement of flap endonuclease 1 in base excision DNA repair", J. Biol. Chem. 273:8842-8848 (1998).

Krasnow et al., "Catenation of DNA by topoisomerases", J. Biol. Chem. 257:2687-2693 (1982).

Kreuzer et al., "Formation and resolution of DNA catenances by DNA gyrase", Cell 20:245-254 (1980).

Laipis et al., "In vitro repair of X-irradiated DNA extracted from Bacillus subtilis deficient in polyemrase I", Proc. Natl. Acad. Sci. USA 69:3211-3214 (1972).

Lieber, "The Fen-1 family of structure-specific nucleases in eukaryotic DNA replication, recombination and repair", BioEssays 19:233-240 (1997).

Mitzel-Landbeck et al., "In vitro repair radiation-induced strand breaks in DNA", Biochem, Biophys. Acta 432:145-153 (1976).

Ranalli et al., "AP endonuclease 1 coordinates flap endonuclease 1 and DNA ligase I activity in long patch base excision repair", J. Biol. Chem. 277:41715-41724 (2002).

Roeder et al., "Isolation of ultrapure supercoiled plasmid-DNA using preparative electrophoresis", Electrophoresis 19:1575-1576 (1998).

Saha et al., "A new method of plasmid DNA preparation by sucrose-mediated detergent lysis from *Escherichia coli* (gram-negative) and *Staphylococcus aureus* (gram-positive)", Anal. Biochem. 176:344-349 (1989).

Seeberg et al., "Base removers and strand scissors: Different Strategies employed in base excision and strand incision at modified base residues in DNA", C.S.H. Symp. Quant. Biol. 65:135-142 (2000).

Seki et al., "A cell-free system for studying a priming factor involved in repair of bleomycin'damaged DNA", (abstract only Acta Med. Okayama 43:73-80 (1989).

Shen et al., "Flap endonuclease homologs in archaebacteria exist as independent proteins", Trends Biochem. Sci. 23:171-173 (1998).

Shlomai et al., "Replication of oX174 DNA with purified enzymes", J. Biol. Chem. 256:5233-5238 (1981).

Vance et al., "Uncoupling of 3'-phosphatase and 5'-kinase functions in budding yeast", J. Biol. Chem. 276:15073-15081 (2001).

Wilson, "Mammalian base excision repair and DNA polymerase beta", Mutation Res. 407:203-215 (1998).

Wilson et al., "DNA polymerase B and mammalian base excision repair", C.S.H. Symp. Quant. Biol. 65:143-155 (2000).

Womble et al., "Method for obtaining more-accurate covalently closed circular plasmid-to-chromosome ratios from bacterial lysates by dye-byoyant density centrifugation", J. Bacteriol. 130:148-153 (1977).

Zhang et al., "Phototriggered formation and repair of DNA containing a site-specific single strand break of the type produced by ionizing radiation or AP lyase activity", Biochemistry 40:153-159 (2001).

Zhixing et al., "DNA gyrase improves DNA transformation of *E. coli* cells with large recombinant plasmids", Nucl. Acids Res. 23:3353-3354 (1995).

Camerini-Otero, R.D. and Felsenfeld, G. "Supercoiling energy and nucleosome formation: the role of the arginine-rich histone kernel", (1977), Nucleic Acids Res., vol. 4, No. 5, pp. 1159-1181.

Champoux and Dulbecco, "An Activity from Mammalian Cells That Untwists Superhelical DNA—A Possible Swivel For DNA Replication"in PNAS, vol. 69, No. 1, pp. 143-146 (1972).

Forterre et al, "High positive supercoiling in vitro catalyzed by an ATP and polyethylene glycol-stimulated topoisomerase from Sulfolobus acidocaldarius", in EMBO Journal, vol. 4, No. 8, pp. 2123-2128 (1985).

LaMarr, et al., "Large scale preparation of positively supercoiled DNA using the archaeal histone HMf", Nucleic Acids Research, 1997, vol. 25, No. 8, pp. 1660-1661.

* cited by examiner

METHOD FOR PLASMID PREPARATION BY CONVERSION OF OPEN CIRCULAR PLASMID TO SUPERCOILED PLASMID

BACKGROUND OF THE INVENTION

Plasmids are double stranded, circular, extrachromosomal DNA molecules (plasmids are defined as such herein). Plasmids are contained inside host cells. One common host cell is *Escherichia coli* (*E. coli*). Many other types of cells are known to carry plasmids. This includes other bacteria, yeast, and higher eukaryotic cells. Plasmids may be artificial (i.e., manmade), such as cloning vectors carrying foreign DNA inserts. Plasmids may also occur naturally, such as in mitochondria and chloroplasts.

Since the invention of cloning circa 1975, the preparation of plasmid has been a routine task in molecular biology. Plasmid preparation has become a highly crowded art. The crowded nature of the art is a reflection of the widespread importance of the procedure in molecular biology. Numerous articles and patents have been published in the past 25 years describing novel methods for preparing plasmid. The problem of plasmid preparation has attracted enormous commercial interest. Companies sell kits for plasmid preparation (Amersham, Qbiogene, Clonetech, Promega, Biorad, Qiagen, Sigma); proprietary resins for purifying plasmid (Qiagen, Amersham, Puresyn, Macherey-Nagel); and automated instruments for preparing plasmid (Qiagen, MacConnell, Autogen).

In the purification of plasmid from host cells, usually bacterial cells, the final plasmid preparation is usually a mixture of two main forms of plasmid: open circular and supercoiled. In the supercoiled form, the plasmid has a covalently closed circular form, and the plasmid is negatively supercoiled in the host cell by the action of host enzymes. In the open circular form, one strand of the DNA duplex is broken at one or more places. The single strand break(s) in an open circular plasmid results in a relaxed topology.

Open circular plasmid in a plasmid preparation can result from several causes. Open circular plasmid may exist in the host cells immediately prior to lysis. Some supercoiled plasmid in the host cells may unintentionally be converted to open circular plasmid in the preparation of a cleared lysate, due to the fragile nature of supercoiled plasmid. Additional plasmid purification procedures, such as organic solvent extraction (e.g. phenol, chloroform), precipitation, ultrafiltration, and chromatography, may unintentionally convert some supercoiled plasmid from the cleared lysate to open circular plasmid, due to the fragile nature of supercoiled plasmid.

Within the context of this invention, unless otherwise indicated or implied, open circular plasmid refers to the open circular plasmid which is commonly present in plasmid preparations after purifying plasmid contained in host cells, and does not refer to open circular plasmid which is purposefully synthesized by an in vitro method. Such purposeful in vitro synthetic methods may be enzymatic or nonenzymatic reactions. Non-limiting examples of purposeful in vitro synthesis of open circular plasmid include purposeful in vitro plasmid replication forming open circular daughter plasmids, open circular plasmid purposefully synthesized from single stranded circular DNA by in vitro enzymatic reactions or synthetic primer annealing, and open circular plasmid produced by purposeful conversion of supercoiled plasmid to open circular plasmid such as purposeful damage with free radicals.

For most plasmid applications, the active plasmid form is supercoiled. Open circular plasmid is often either inactive or poorly active. Plasmid for gene transfer (e.g. in vitro DNA transformation or in vivo DNA therapy) may require a high percentage of supercoiled plasmid and a low percentage of open circular plasmid contamination. Numerous methods have been described in the prior art to achieve this objective.

Le Brun et al. described a method for purifying supercooled plasmid from open circular plasmid using agarose gel electrophoresis (BioTechniques 6:836-838, 1988). Separation was based on differential migration in agarose gel. Supercoiled plasmid was recovered from the ethidium bromide stained gel. Hediger described a similar method using continuous elution (Anal. Biochem. 159:280-286, 1986).

Gorich et al. described a method for purifying supercoiled plasmid from open circular plasmid using polyacrylamide gel electrophoresis (Electrophoresis 19:1575-1576, 1998). Separation was based on differential migration in polyacrylamide gel. Supercoiled plasmid was recovered from the gel by electrophoretic elution.

Womble et al. described a method for purfying supercoiled plasmid using density gradient centrifugation (J. Bacteriol. 130:148-153, 1977). Plasmid was dissolved in a cesium chloride-ethidium bromide solution and centrifuged at high speed. Supercoiled plasmid was separated from open circular plasmid based on differential incorporation of ethidium bromide.

Best et al. described a method for purifying supercoiled plasmid using reverse phase chromatography (Anal. Biochem. 114:235-243, 1981). The chromatographic resin separated supercoiled from open circular forms. Many chromatographic methods have been described in the prior art for separating supercoiled plasmid from open circular plasmid. This includes reverse phase, anion exchange, size exclusion, membrane, and thiophilic chromatography. Several chromatographic resins are commercially available for separating supercoiled from open circular forms (Puresyn, Amersham, Prometic).

Hyman described a method for purifying supercoiled plasmid using selective exonuclease digestion (BioTechniques, 13:550-554, 1992). A cell lysate was incubated with a mixture of exonuclease I and exonuclease III. The exonucleases selectively degraded open circular plasmid and chromosomal DNA without degrading supercoiled plasmid, thereby purifying supercoiled plasmid.

Prior art methods for purifying supercoiled plasmid from open circular plasmid involve separation and removal of open circular plasmid from supercoiled plasmid, or selective degradation of the open circular plasmid. In the chromatographic, electrophoretic, and ultracentrifugation prior art methods for purifying supercoiled plasmid, the open circular plasmid is separated and removed. In the enzymatic prior art methods, open circular plasmid is selectively degraded by exonuclease. One disadvantage of prior art approaches is that the final yield of supercoiled plasmid is reduced because open circular plasmid is removed or degraded.

The invention overcomes the inherent disadvantage of prior art methods by using a fundamentally different operating principle, by converting open circular plasmid to supercoiled plasmid. This invention provides an improved method for plasmid preparation.

SUMMARY OF THE INVENTION

An objective of the invention is to provide a method for preparing supercoiled plasmid, by converting open circular plasmid into supercoiled plasmid enzymatically, thereby achieving a plasmid preparation which has an increased proportion of supercoiled plasmid.

In one embodiment of the invention, a method is provided for preparing plasmid from host cells which contain the plasmid, comprising: (a) providing a plasmid solution comprised of unligatable open circular plasmid; (b) reacting the unligatable open circular plasmid with one or more enzymes and appropriate nucleotide cofactor(s), such that at least some unligatable open circular plasmid is converted to 3'-hydroxyl, 5'-phosphate nicked plasmid; (c) reacting the 3'-hydroxyl, 5'-phosphate nicked plasmid with a DNA ligase and DNA ligase nucleotide cofactor, such that at least some 3'-hydroxyl, 5'-phosphate nicked plasmid is converted to relaxed covalently closed circular plasmid; and (d) reacting the relaxed covalently closed circular plasmid with a DNA gyrase and DNA gyrase nucleotide cofactor, such that at least some relaxed covalently closed circular plasmid is converted to negatively supercoiled plasmid. In other embodiments, DNA gyrase is replaced with reverse DNA gyrase or reaction (d) is not performed. Incubations may also include salt, buffer, and nucleotide cofactor appropriate for the enzyme. Reaction conditions such as concentration of the aforementioned chemicals, temperature, and time may be adjusted to provide suitable conversion kinetics and yield.

Preferably, reactions (b), (c), and (d) are performed in a single reaction using an enzyme mixture comprising a DNA polymerase, DNA ligase, and DNA gyrase. Preferably, the mixture further comprises a 3' deblocking enzyme. Preferably, the mixture further comprises a kinase enzyme and a high energy phosphate donor, which converts the nucleotide by-product of DNA gyrase nucleotide cofactor back to nucleotide cofactor. Preferably, the enzyme mixture further comprises one or more exonucleases, which degrades linear chromosomal DNA.

Further embodiments of the invention include kits and compositions comprising one or more of the aforementioned enzymes. In a kit, enzymes in one or more containers (separate enzyme compositions or a mixture thereof) may be packaged for single or multiple reactions. Instructions for practicing a method of the invention are another optional component of the kit. Instructions may be a printed sheet included in the kit or a label applied to the outside of the kit.

Further objectives and advantages will become apparent from a consideration of the ensuing description.

DESCRIPTION OF SPECIFIC EMBODIMENTS OF THE INVENTION

In the invention, open circular plasmid is enzymatically converted to supercoiled plasmid. This is accomplished by incubating the open circular plasmid with enzymes, either sequentially or preferably simultaneously with an enzyme mixture. The result of this enzymatic incubation is a plasmid preparation with a higher percentage of supercoiled plasmid and a lower percentage of open circular plasmid. The invention operates in a fundamentally different manner from the prior art.

Preparing the Cleared Lysate

The enzymatic conversion reactions (conversion reactions) of the invention are preferably performed after obtaining a cleared lysate of host cells containing the plasmid. A "cleared lysate" is a well known term in the art and refers to an aqueous solution containing plasmid, and usually RNA, usually soluble proteins, and usually residual amounts of chromosomal DNA, which is obtained after lysis of host cells and the separation of the cell debris, usually by filtration or centrifugation. Any method for preparing a cleared lysate may be potentially useful. Plasmid in the cleared lysate is usually a mixture of supercoiled and open circular plasmid.

The host cells containing plasmid are preferably bacteria, preferably *Escherichia coli*. Two methods are commonly used in the art for producing a cleared lysate from bacteria. Both methods comprise lysing the host cells, precipitating chromosomal DNA, and removing the precipitated chromosomal DNA and cell debris, usually by centrifugation and/or filtration. In the alkaline lysis method (e.g. Birnboim, Nucl. Acids Res. 7:1513-1523, 1975), host cells are lysed using an alkaline solution. Chromosomal DNA is precipitated by adding an acidic solution to (or neutralizing) the lysed cell solution. The precipitated chromosomal DNA and cell debris is usually removed by filtration or centrifugation. In the boiling method (e.g. Holmes, Anal. Biochem. 114:193-197, 1981), host cells are usually lysed using lysozyme. Chromosomal DNA is precipitated by heating the lysed cell solution; the precipitated chromosomal DNA and cell debris is usually removed by centrifugation. Other non-limiting methods of potential use for preparing a cleared lysate may include mechanical disruption methods (U.S. Pat. No. 6,455,287). Preferably, the cleared lysate is prepared by a process which separates host cell chromosomal DNA from the plasmid. A preferred method for preparing a cleared lysate is the alkaline lysis method.

After preparing the cleared lysate, the plasmid in the cleared lysate is optionally further purified from other host cell components in any desired manner prior to the conversion reactions. Further purification can be accomplished by many methods, such as organic solvent extraction, precipitation, RNA digestion by a ribonuclease, chromatography, electrophoresis, ultrafiltration (e.g. tangential flow ultrafiltration), or combinations thereof. Preferably, the further purification procedure(s) do not separate open circular plasmid from supercoiled plasmid or degrade open circular plasmid. Further purification may be advantageous. Further purification may result in plasmid in a buffer which is more suitable for the conversion reactions. Further purification may allow more efficient and reliable conversion reactions by removing contaminants (such as protein and RNA) which might inhibit the conversion reactions. Preferably, the plasmid solution is prepared by a process which separates host cell chromosomal DNA from the plasmid. Preferably, the plasmid solution is obtained by a process which does not purposefully separate open circular plasmid from supercoiled plasmid. Preferably, the plasmid solution is obtained by a process which does not purposefully degrade open circular plasmid.

After preparing a cleared lysate, and optionally further purifying the plasmid from other host cell components, the resulting plasmid solution comprises open circular plasmid, and usually supercoiled plasmid (i.e., usually a mixture of open circular and supercoiled plasmids).

Enzymatic Conversion Reactions

The inventor has discovered that the vast majority of open circular plasmid in plasmid preparations is unligatable (defined as open circular plasmid which is not 3'-hydroxyl, 5'-phosphate nicked plasmid), which cannot be converted to relaxed covalently closed circular form using only DNA ligase. Only a small amount of open circular plasmid is 3'-hydroxyl, 5'-phosphate nicked plasmid. This is an unexpected and surprising observation, as the prior art would predict that about half of the open circular plasmid would be 3'-hydroxyl, 5'-phosphate nicked plasmid. However, this is not observed experimentally for open circular plasmid in plasmid preparations.

The enzymatic conversion reactions (conversion reactions) are preferably performed on open circular plasmid in the plasmid solution. One embodiment of the invention preferably comprises three enzymatic conversion reactions, which convert unligatable open circular plasmid to supercoiled plasmid. They may be performed sequentially or simultaneously.

First Enzymatic Reaction: Conversion of Unligatable Open Circular Plasmid to 3'-Hydroxyl, 5'-Phosphate Nicked Plasmid.

In the first enzymatic conversion reaction (first reaction), unligatable open circular plasmid in a plasmid solution is converted in vitro to 3'-hydroxyl, 5'-phosphate nicked plasmid (ligatable form). This is accomplished by incubation with one or more enzymes in the presence of appropriate cofactor(s) (if necessary), usually nucleotide cofactor(s). Preferably, a purified form of the enzyme(s) is used in this reaction (M. Deutscher, Methods in Enzymology: Guide to Protein Purification, vol. 182, Academic Press, 1990), such as chromatographically purified. This reaction can be accomplished by two methods.

Preferred Mode: In a preferred conversion method, the unligatable open circular plasmid is converted to 3'-hydroxyl, 5'-phosphate nicked plasmid by incubation with a DNA polymerase (i.e. an enzyme having DNA template dependent 5'-3' DNA polymerase activity) in the presence of DNA polymerase cofactor substrate(s), usually nucleotide substrate(s), preferably deoxyribonucleoside triphosphate substrate(s) (dNTPs). Preferably, a purified form of the DNA polymerase is used, such as chromatographically purified.

A preferred polymerase is DNA polymerase I, which preferably has both 3'-5' and 5'-3' exonuclease activities. The 5'-3' exonuclease activity of DNA polymerase I may advantageously convert some 5' termini of open circular plasmid that lack a 5'-phosphate to a 5'-phosphate terminus. This activity is also known as nick translation. The 3'-5' exonuclease activity of DNA polymerase I may advantageously convert some 3' termini of open circular plasmid that lack a 3'-hydroxyl to a 3'-hydroxyl. The inventor has observed that DNA polymerase I, in the presence of dNTPs, is able to convert most of the unligatable open circular plasmid to 3'-hydroxyl, 5'-phosphate nicked plasmid. Example 1 demonstrates non-limiting embodiments of the preferred mode. Other DNA polymerases may be used.

A 3' deblocking enzyme may optionally be used to assist in the first reaction. Some unligatable open circular plasmid may have a blocking group at the 3' terminus. The blocking group may inhibit (completely or partially) the ability of DNA polymerase to extend the 3' terminus. In this case, a 3' deblocking enzyme may remove the 3' blocking group and produce a 3'-hydroxyl terminus. The resulting 3'-hydroxyl terminus may then be extended by DNA polymerase. Incubations with 3' deblocking enzyme and DNA polymerase are preferably performed simultaneously, but could also be performed sequentially in the order 3' deblocking enzyme followed by DNA polymerase. Preferably, a purified form of the 3' deblocking enzyme is used, such as chromatographically purified. Non-limiting examples of 3' deblocking enzymes may include a non-processive or low processivity double stranded DNA 3'-5 exonucleases, single strand cutting endonucleases (e.g. AP endonucleases), 3'-phosphodiesterase, and phosphatases, and are discussed below.

A preferred 3' deblocking enzyme is a non-processive or low processivity double stranded DNA 3'-5' exonuclease, such as preferably exonuclease III. Exonuclease III converts 3'-blocked open circular plasmid to 3'-hydroxyl gapped plasmid. Exonuclease III has four activities, all of which may serve a 3' deblocking function: 3'-5' exonuclease activity, 3'-phosphatase activity, apurinic/apyrimidinic (AP) endonuclease activity and 3'-phosphodiesterase. When coincubated with DNA polymerase, the ratio of exonuclease III and DNA polymerase activities should be balanced appropriately to avoid significant exonuclease degradation of open circular plasmid. Exonuclease III from any source may be useful. Exonuclease III is likely found in many organisms. A preferred source of exonuclease III is $E.\ coli$. Other non-processive or low processivity double stranded DNA 3'-5' exonucleases may also serve as a 3' deblocking enzyme. It will be appreciated that high processivity double stranded 3'-5' exonucleases would not be useful as 3'-deblocking enzymes, as such exonucleases would completely, or substantially completely, degrade open circular plasmid to single stranded circular DNA prior to dissociating from the substrate.

Another useful 3' deblocking enzyme is a single strand cutting endonuclease, such as preferably AP endonuclease (or an enzyme with AP endonuclease activity). AP endonuclease converts AP sites in open circular plasmid to 3' hydroxyl gapped plasmid. AP endonucleases are found in many organisms. AP endonuclease from any source may be used. A preferred AP endonuclease is endonuclease IV. A preferred source of endonuclease IV is $E.\ coli$. Another useful AP endonuclease may be APE1 (Ranalli, J. Biol. Chem. 277: 41715-41724, 2002; Izumi et al. Carcinogenesis 21:1329-1334, 2000). Other AP endonucleases or other types of single strand cutting endonucleases may also serve as 3' deblocking enzymes. Exonuclease III is usually also an AP endonuclease.

Another useful 3' deblocking enzyme is phosphatase, such as preferably 3'-phosphatase. 3'-Phosphatase efficiently dephosphorylates a 3'-phosphate blocking group to 3'-hydroxyl terminus. Another useful 3'-phosphatase 3'-deblocking enzyme is polynucleotide kinase—3'-phosphatase (PNKP). In addition to the 3'-phosphatase activity, the polynucleotide kinase activity of PNKP is able to convert 5'-hydroxyl termini to 5'-phosphate termini. Other phosphatases may also be useful.

Other 3' deblocking enzymes can potentially be used provided that they convert the blocked 3' terminus of open circular plasmid to a 3' hydroxyl terminus. More than one 3' deblocking enzyme may be used during the first reaction. A 3' deblocking enzyme may be especially advantageous when used with a DNA polymerase which lacks 3'-5 exonuclease activity. A 3' deblocking enzyme may be used with a DNA polymerase which has 3'-5' exonuclease activity, possibly enhancing repair efficiency. Example 2 demonstrates non-limiting embodiments using 3' deblocking enzymes. Example 2 demonstrates that the 3' deblocking enzymes can enhance the conversion efficiency.

A 5'deblocking enzyme may optionally be used to assist in the first reaction. The 5' deblocking enzyme converts a blocked 5'-terminus of open circular plasmid to a 5'-phosphate terminus. The 5' deblocking enzyme may be able to remove 5' blocking groups which DNA polymerase is unable to remove. A preferred 5' deblocking enzyme is flap endonuclease, an enzyme which has been reported to be homologous to the 5'-3' exonuclease of DNA polymerase I. In eukaryotes and archaeabacteria, DNA polymerase and flap endonuclease are reported to be employed for repair of some single strand breaks (Lieber, Bioessays 19:233-240, 1997; Kim, J. Biol. Chem. 273:8842-8848, 1998; Shu, Trends Biochem Sci. 23:171-173, 1998). Incubation with 5' deblocking enzyme and DNA polymerase are preferably performed simultaneously, but could potentially also be performed sequentially in the order: 5' deblocking enzyme followed by DNA polymerase. Preferably, a purified form of the 5' deblocking enzyme is used, such as chromatographically purified. Non-limiting examples of 5' deblocking enzymes of potential use may include non-processive or low processivity 5'-3' exonucleases, AP lyases, flap endonucleases or flap exonucleases (such as FEN1 or T5 exonuclease), and DNA deoxyribophosphodiesterases. These enzymes are well characterized in the art of DNA repair (Friedberg et al., DNA Repair and Mutagenesis, ASM Press, 1995). Other 5' deblocking enzymes may potentially be used provided that they convert a blocked 5' terminus of open circular plasmid to a 5' phosphate terminus.

A 5' deblocking enzyme may advantageously reduce unintentional strand displacement side reactions of DNA polymerase or remove the displaced strand. A 5' deblocking enzyme may possibly also selectively digest some linear chromosomal DNA. More than one 5' deblocking enzyme may be used in the first reaction. A 5' deblocking enzyme may be especially advantageous when used with a DNA polymerase which lacks 5' terminus repair activity, such as 5'-3' exonuclease activity. A 5' deblocking enzyme may be used with a DNA polymerase which has 5' terminus repair activity, possibly enhancing repair efficiency. The first reaction may optionally employ both 5' and 3' deblocking enzymes, simultaneously or in any order, but preferably simultaneously with DNA polymerase incubation.

It will be appreciated that having repair capacity for both 3' and 5' termini of open circular plasmid is preferable to maximize the conversion efficiency, using either the inherent repair activity of the DNA polymerase (such as 3'-5' exonuclease for the 3' terminus; such as 5'-3' exonuclease or lyase for the 5' terminus) or a deblocking enzyme or both. This may be accomplished in the following manners:

(1) Preferably, the DNA polymerase has both 3' and 5' terminus repair activities (e.g. some DNA polymerase I enzymes). In this case, a 3' deblocking or 5' deblocking enzyme or both may optionally be added to possibly enhance repair efficiency.

(2) If the DNA polymerase lacks 3' terminus repair activity and has 5' terminus repair activity (e.g. Taq DNA polymerase, some eukaryotic DNA polymerases), then preferably the first reaction is performed using DNA polymerase and a 3' deblocking enzyme. In this case, a 5' deblocking enzyme may optionally be added to possibly enhance repair efficiency. For eukaryotic DNA polymerases, the 5' deblocking enzyme flap endonuclease may be especially advantageous in assisting the inherent 5' terminus lyase repair activity of some eukaryotic DNA polymerases, such as DNA polymerase beta (Wilson, Mut. Res. 407:203-215, 1998; Wilson, Mut. Res. 460:231-244, 2000). For example, the first reaction may be performed using AP endonuclease, DNA polymerase beta, and optionally flap endonuclease (Wilson; C. S. H. Symp. Quant. Biol. LXV: 143-155, 2000).

(3) If the DNA polymerase has 3' terminus repair activity and lacks 5' terminus repair activity (e.g. some phage DNA polymerases), then preferably the first reaction is performed using DNA polymerase and 5' deblocking enzyme. In this case, a 3' deblocking enzyme may optionally be added to possibly enhance repair efficiency.

(4) If the DNA polymerase lacks both 3' and 5' terminus repair activities (e.g. reverse transcriptase or mutant DNA polymerases), then preferably the first reaction is performed using DNA polymerase, 3' deblocking enzyme, and 5' deblocking enzyme.

For any given DNA polymerase, a person skilled in the art may optionally select appropriate 3' deblocking and/or 5' deblocking enzymes based on the known enzyme activities of the DNA polymerase, the known in vivo system of the DNA polymerase for single strand break repair, and the desired conversion efficiency of open circular to supercoiled plasmid. It will be appreciated that some DNA polymerases may be advantageous if the DNA polymerase functions in vivo in DNA repair. Preferably, at least one repair activity is provided in the first reaction for both the 3' terminus and the 5' terminus of open circular plasmid, using either the repair activity from the DNA polymerase or a deblocking enzyme or both.

Using the preferred mode of the first reaction, most or nearly all unligatable open circular plasmid can be converted to 3'-hydroxyl, 5'-phosphate nicked plasmid.

Alternate Mode: In an alternate conversion method, the unligatable open circular plasmid is incubated with polynucleotide kinase and 3'-phosphatase in the presence of nucleotide cofactor, preferably using the enzyme PNKP. PNKP converts unligatable open circular plasmid which is 3'-phosphate, 5'-hydroxyl nicked plasmid to 3'-hydroxyl, 5'-phosphate nicked plasmid. The incubations with 3'-phosphatase and polynucleotide kinase are preferably performed simultaneously using PNKP, but could also be performed sequentially in any order. Preferably, a purified form of the 3'-phosphatase and polynucleotide kinase are used, such as chromatographically purified. Example 6 demonstrates a non-limiting embodiment of the alternate mode.

Using the alternate mode of the first reaction, at least some of the unligatable open circular plasmid can be converted to 3'-hydroxyl, 5'-phosphate nicked plasmid.

Other Modes: Any method for converting unligatable open circular plasmid to 3'-hydroxyl, 5'-phosphate nicked plasmid may be used. Other methods may be provided using the many enzymes and methods known in the art of DNA repair (Friedberg et al., DNA Repair and Mutagenesis, ASM Press, 1995).

Second Enzymatic Reaction: Conversion of 3'-hydroxyl, 5'-phosphate Nicked Plasmid to Relaxed Covalently Closed Circular Plasmid.

In the second enzymatic conversion reaction (second reaction), the 3'-hydroxyl, 5'-phosphate nicked plasmid is converted in vitro to relaxed covalently closed circular plasmid. This is accomplished by incubation with a DNA ligase (i.e. an enzyme having 3'-hydroxyl, 5'-phosphate nicked DNA ligase activity) in the presence of DNA ligase cofactor substrate, usually nucleotide cofactor, usually ATP or NAD or analog. Preferably, a purified form of the DNA ligase is used, such as chromatographically purified.

Third Enzymatic Reaction: Conversion of Relaxed Covalently Closed Circular Plasmid to Negatively Supercoiled Plasmid.

In the third enzymatic conversion reaction (third reaction), the relaxed covalently closed circular plasmid is converted in vitro to negatively supercoiled plasmid. This is accomplished by incubation with a DNA gyrase (i.e. an enzyme having DNA gyrase activity) in the presence of DNA gyrase cofactor substrate, usually nucleotide cofactor, usually ATP or analog. Preferably, a purified form of the DNA gyrase is used, such as chromatographically purified.

The repair of open circular plasmid in a plasmid preparation has not been previously demonstrated experimentally. The nature of the DNA damage in open circular plasmid in plasmid preparations has not been investigated in the literature. To date, no one has experimentally demonstrated that this open circular plasmid can be converted to supercoiled plasmid in vitro. This is the first demonstration that such open circular plasmid can be converted in vitro. Surprisingly and unexpectedly, in the preferred mode, the conversion of open circular plasmid to supercoiled plasmid may be nearly quantitative. Nearly all of the open circular plasmid may be converted to supercoiled plasmid.

Performing the Enzymatic Conversion Reactions

The three enzymatic conversion reactions are preferably performed simultaneously in a single combined incubation, using an enzyme mixture. In a preferred mode, the enzyme mixture may comprise DNA polymerase, DNA ligase, and DNA gyrase. This mixture may further comprise one or more 3' deblocking enzymes. This mixture may further comprise one or more 5' deblocking enzymes. In an alternate mode, the enzyme mixture may comprise 3'-phosphatase, polynucleotide kinase, DNA ligase, and DNA gyrase. By using a single combined incubation, open circular plasmid unintentionally generated during an incubation (e.g. by an enzyme contaminant) may be converted to supercoiled plasmid. Alternatively, the three conversion reactions may also be performed sequentially in the order: first reaction, second reaction, and third reaction. Alternatively, the first and second reactions may be performed simultaneously, followed by the third reaction. Alternatively, the first reaction may be performed, followed by the second and third reactions simultaneously. If the optimal incubation conditions, such as temperature or pH or buffer conditions, differ for the enzymes used herein, it may be advantageous to perform the conversion reactions sequentially.

The conversion reactions may be performed with intermediate purification of plasmid between conversion reactions. A disadvantage of such intermediate purification embodiments is that a substantial amount of plasmid may be lost in the intermediate purification. Preferably, the conversion reactions are performed without intermediate purification of plasmid.

Preferably, the conversion reactions convert at least 50%, at least 60%, at least 70%, at least 80%, at least 90%, or at least 95% of open circular plasmid in the plasmid solution to supercoiled plasmid. Preferably, after the conversions reactions, at least 70%, at least 80%, at least 90%, or at least 95% of total plasmid is in supercoiled form.

For some applications, relaxed covalently closed circular plasmid may have the same bioactivity as supercoiled plasmid or conversion of relaxed covalently closed circular plasmid to supercoiled plasmid may not be necessary or desired. In this case, the third reaction with DNA gyrase may be omitted. In this embodiment, preferably the first and second reactions convert at least 50%, at least 60%, at least 70%, at least 80%, at least 90%, or at least 95% of open circular plasmid in the plasmid solution to relaxed covalently closed circular plasmid. In this embodiment, preferably after the second reaction, at least 70%, at least 80%, at least 90%, or at least 95% of total plasmid is in covalently closed circular form. In one embodiment, the second reaction may be performed with DNA ligase in the presence of an intercalating agent, followed by removal of the intercalating agent after the ligation reaction, resulting in negatively supercoiled plasmid. Preferably however, the second reaction is performed in the absence of an intercalating agent, due to the potential carcinogenic nature of some intercalating agents.

Enzymes

3'-Phosphatase and polynucleotide kinase enzymes from any source may be used provided that they are active on open circular plasmid substrate. Polynucleotide kinase and 3'-phosphatase enzyme activities are sometimes found on a single polypeptide in some organisms, known as PNKP. PNKP has been characterized in numerous organisms, including rats, human, bovine, plasmodium, *S. pombe,* and mouse (Karimi-Busheri et al., Nucl. Acids Res. 26:4395-4400, 1998). 3'-Phosphatase with no associated polynucleotide kinase activity has been characterized in *Saccharomyces cereviseae* and *Arabidopsis thaliana* (Vance et al., J. Biol. Chem. 276:15073-15081, 2001). Polynucleotide kinase with no associated 3'-phosphatase could potentially be obtained by mutation of PNKP. The polynucleotide kinase and 3'-phosphatase enzymes may be present on separate proteins, but preferably are present on the same protein (PNKP). A preferred source of PNKP is human.

DNA polymerase from any source may be useful: e.g. Klenow DNA polymerase, eubacterial DNA polymerases, phage DNA polymerases, viral DNA polymerases such as reverse transcriptase, eukaryotic DNA polymerases, archaebacterial DNA polymerases, and genetically mutated versions thereof. Preferably, the DNA polymerase does not have substantial strand displacing activity on open circular plasmid. A preferred DNA polymerase has both 3'-5' and 5'-3' exonuclease activities, such as DNA polymerase I from some sources. More than one DNA polymerase may be used in the first reaction. DNA polymerase I is likely found in many organisms. A preferred source of DNA polymerase I is *E. coli.* Preferably, four DNA polymerase nucleotide substrates are used with DNA polymerase in the first reaction, such as DATP, dGTP, dCTP, and dTTP (or analogs). In other embodiments, less than four nucleotide substrates could be used, for example if a nucleotide substrate can be incorporated by DNA polymerase opposite more than one template base.

DNA ligase from any source may be used, provided that it is capable of ligating 3'-hydroxyl, 5'-phosphate nicks. DNA ligase is found in many organisms. DNA ligases from bacteriophages, viruses, eukaryotes, and archaebacteria usually can use adenosine triphosphate (ATP) as the nucleotide cofactor. DNA ligases from eubacteria, such as *E. coli,* usually can use nicotinamide adenine dinucleotide (NAD) as the cofactor. More than one DNA ligase may be used in the second reaction. Preferably, the DNA ligase is able to use ATP as nucleotide substrate cofactor. A preferred source of DNA ligase is bacteriophage, such as T4.

DNA gyrase from any source can be used, provided that it converts relaxed covalently closed circular plasmid to negatively supercoiled plasmid. DNA gyrase is found in eubacteria and likely some archeabacteria. DNA gyrase converts relaxed covalently closed circular plasmid to negatively supercoiled plasmid in the presence of ATP or an equivalent nucleotide (e.g. ATP analog). A preferred source of DNA gyrase is *E. coli.* Another useful source of DNA gyrase could be *Vibrio cholera,* which is reported to be unable to catalyze the reverse reaction (Mukhopadhyay et al., Biochemical J. 280:797-800, 1991). Another useful source of DNA gyrase could be *mycobaterium smegmatis,* which is reported to have stronger decatenase activity. More than one DNA gyrase may be used in the third reaction. The incubation with DNA gyrase is preferably performed substantially in the absence of topoisomerase I.

Reverse DNA gyrase (i.e. an enzyme with reverse DNA gyrase activity) may be used instead of DNA gyrase. Reverse DNA gyrase is found in many thermophilic bacteria. Reverse DNA gyrase converts relaxed covalently closed circular plasmid to positively supercoiled plasmid. The use of reverse DNA gyrase would produce a plasmid preparation with positively supercoiled plasmid. In this embodiment, preferably the conversion reactions convert at least 50%, at least 60%, at least 70%, at least 80%, at least 90%, or at least 95% of open circular plasmid in the plasmid solution to positively supercoiled plasmid. Preferably in this embodiment, after the conversions reactions, at least 70%, at least 80%, at least 90%, or at least 95% of total plasmid is in positively supercoiled form. Preferably, however, DNA gyrase is employed, because negatively supercoiled plasmid is known to be biologically active in human cells. In another embodiment, a kit could supply both DNA gyrase and reverse DNA gyrase, allowing the user to select the desired gyrase.

Repair Enzymes and Accessory Proteins

The repair of single strand breaks in double stranded DNA is an essential function of the DNA repair system of all living organisms. Numerous repair enzymes and accessory proteins are known which facilitate the repair of single strand breaks. Such enzymes and accessory proteins could be used to accelerate or improve the conversion of unligatable open circular plasmid to covalently closed circular plasmid. Non-limiting examples of other proteins/enzymes of potential use in repairing single stranded breaks in open circular plasmid may include protein HU, XRCC1, RNase H,0 DNA glycosylases, damage-specific endonucleases (e.g. UvrABC), and enzymes involved in single strand break repair, base excision repair, nucleotide excision repair, or mismatch repair (Friedberg et al., DNA Repair and Mutagenesis, ASM Press, 1995).

Optional Nucleotide Cofactor Regeneration

Several enzymes used herein require nucleotide cofactors. DNA gyrase and polynucleotide kinase usually can use ATP (or analog) as the cofactor, generating ADP (or analog) as the nucleotide by-product of the cofactor. DNA ligase usually can use ATP or NAD (or analog) for activity, generating AMP or NMP (or analog) as the nucleotide by-product of the cofactor. It will be appreciated that equivalent cofactors may potentially be used (e.g. DATP). Optionally, the nucleotide by-product of the cofactor may be enzymatically converted back to nucleotide cofactor during one or more of the reactions, thus, helping to maintain a constant concentration of nucleotide cofactor.

Optionally during the third reaction, the nucleotide by-product of DNA gyrase nucleotide cofactor (usually ADP or analog) generated by DNA gyrase may be converted back to nucleotide cofactor (usually ATP or analog) using a kinase enzyme and a high energy phosphate donor (i.e., the kinase substrate). The preferred kinase enzyme and phosphate donor are pyruvate kinase and phosphoenolpyruvate (PEP). Other non-limiting kinase and high energy phosphate donors may include creatine kinase and creatine phosphate, and acetate kinase and phosphoacetate. Preferably, a purified form of the kinase enzyme is used, such as chromatographically purified.

Optionally during the first reaction, the nucleotide by-product of polynucleotide kinase nucleotide cofactor (usually ADP or analog) generated by polynucleotide kinase may be converted back to nucleotide cofactor (usually ATP or analog) using a kinase enzyme and a high energy phosphate donor.

Optionally during the second reaction, the nucleotide by-product of DNA ligase nucleotide cofactor (e.g. AMP or analog) generated by DNA ligase may be converted back to nucleotide cofactor (e.g. ATP or analog) using a mixture of adenylate kinase, kinase enzyme, and high energy phosphate donor. If the cofactor for DNA ligase is NAD, the nucleotide by-product NMP may be converted back to NAD during the second reaction by the enzyme nicotinamide adenylyltransferase. AMP generated by this ligase may be converted back to ATP as described. Preferably, a purified form of the kinase enzyme and adenylate kinase are used, such as chromatographically purified.

Pyrophosphate is usually generated as a by-product of the DNA ligase and the DNA polymerase reactions. Optionally, inorganic pyrophosphatase may be included during the incubation with DNA ligase and/or DNA polymerase, to hydrolyze pyrophosphate to phosphate. Preferably, a purified form of the inorganic pyrophosphatase is used, such as chromatographically purified.

The use of enzymes for regenerating nucleotide cofactor from their nucleotide by-product is optional. Example 3 demonstrates a non-limiting embodiment using ATP regeneration.

Optional Exonuclease Reaction

An optional additional in vitro enzymatic reaction with one or more exonucleases may be performed to reduce linear chromosomal DNA contamination in the plasmid solution. Linear chromosomal DNA may be in single stranded form, double stranded form, other possible forms, or a mixture. The linear chromosomal DNA may be reacted with one or more exonucleases, wherein said exonucleases have at least some substrate selectivity in preferentially degrading linear chromosomal DNA substrate versus covalently closed circular plasmid, whereby at least some linear chromosomal DNA is degraded. Within the context of the invention, an exonuclease is defined as an enzyme having at least some substrate selectivity in preferentially degrading linear DNA substrate (single stranded or double stranded or both) versus covalently closed circular plasmid. The exonuclease reaction is preferably performed without substantially hydrolyzing covalently closed circular plasmid. In some embodiments, the exonuclease reaction may also advantageously degrade open circular plasmid which is remaining after the second reaction. It will be appreciated that the selectivity of the exonucleases need not be absolute. Most exonucleases lack absolute substrate specificity. A loss of plasmid due to lack of absolute substrate specificity by an exonuclease may be necessary to achieve desired reduction in chromosomal DNA. Preferably, a purified form of the exonuclease(s) is used, such as chromatographically purified. Preferably, the exonuclease reaction will reduce chromosomal DNA contamination to less than 2%, less than 1%, less than 0.5%, or less than 0.1% of plasmid DNA. Preferably, the exonuclease reaction degrades at least 5%, at least 10%, at least 25%, at least 50%, at least 75%, at least 90%, or at least 95% of the linear chromosomal DNA in the plasmid solution. A person skilled in the art may select exonuclease(s) to achieve the desired reduction in chromosomal DNA.

The preferred selection of the exonuclease(s) depends on when the reaction is performed. Preferably, if the exonuclease reaction is performed prior to completing the second reaction, the linear chromosomal DNA may be reacted with one or more exonucleases, wherein said exonucleases have at least some substrate selectivity in preferentially degrading linear chromosomal DNA substrate versus open circular and covalently closed circular plasmid, whereby at least some linear chromosomal DNA is degraded. This exonuclease reaction is preferably performed without substantially hydrolyzing open circular and covalently closed circular plasmid. Non-limiting examples of such exonucleases may include exonuclease I, lambda exonuclease, exonuclease V, exonuclease VII, exonuclease VIII, exonuclease T (RNase T), recJf, or combinations thereof. Such exonucleases may be conveniently used concurrently with all the conversion reactions. In addition, deblocking enzymes which are also exonucleases may potentially serve a dual function of hydrolyzing chromosomal DNA. Some plasmid (such as open circular plasmid or closed circular plasmid) may be degraded due to a lack of absolute exonuclease substrate specificity. The optional exonuclease reaction is preferably performed concurrently with the conversion reactions, preferably using exonuclease V, preferably with low helicase activity. A preferred source of exonuclease V is *M. luteus*. The nucleotide by-product of exonuclease V nucleotide cofactor (usually ADP or analog) generated by exonuclease V may be converted back to nucleotide cofactor (usually ATP or analog) as described. Example 4 demonstrates non-limiting embodiments using concurrent exonuclease digestion.

Preferably, if the exonuclease reaction is performed after the second reaction, the linear chromosomal DNA may be reacted with one or more exonucleases, wherein said exonucleases have at least some substrate selectivity in preferentially degrading linear chromosomal DNA substrate versus covalently closed circular plasmid, whereby at least some linear chromosomal DNA is degraded. This exonuclease reaction is preferably performed without substantially hydrolyzing covalently closed circular plasmid. Non-limiting examples of such exonucleases may include exonuclease I, exonuclease III, exonuclease V, exonuclease VII, exonuclease VIII, lambda exonuclease, T7 exonuclease, T5 exonuclease, exonuclease T, RecJf, or combinations thereof. The 3'-5' exonuclease activity of DNA polymerase may be used as an exonuclease in the absence of nucleotide substrate, e.g. dNTP substrate. Such exonucleases may be conveniently used subsequent to the conversion reactions. Some covalently closed circular plasmid may be degraded by the exonuclease reaction due to a lack of absolute exonuclease substrate specificity. The conversion of open circular plasmid to covalently closed circular plasmid in the conversion reactions will usually not be 100%, resulting in remaining open circular plasmid after the second reaction. In one embodiment, after the second reaction, this exonuclease reaction may also advantageously degrade remaining open circular plasmid. This is accomplished using an exonuclease which degrades open circular plasmid, for example using T7 exonuclease or exonuclease III. If DNA polymerase and dNTPs are present during this exonuclease digestion using exonuclease III, then the concentration of exonuclease III should be adjusted appropriately to effect digestion of linear double stranded chromosomal DNA. Alternatively, DNA polymerase (and/or other enzymes used in the conversion reactions) may optionally be inactivated or removed prior to the subsequent exonuclease digestion, such as by heat inactivation. Example 5 demonstrates a non-limiting embodiment using subsequent exonuclease digestion.

The amount of plasmid degraded during the exonuclease reaction may depend on several factors, such as substrate specificity of the exonuclease(s), whether the exonuclease(s) are used to remove remaining open circular plasmid after the second reaction and the amount of remaining open circular plasmid, and reaction conditions (enzyme concentrations, incubation times, etc). The plasmid loss is preferably not substantial; however, in some cases, the loss may be substantial. For example, plasmid loss may be substantial if a large amount of open circular plasmid is remaining after the second reaction, and this remaining open circular plasmid is degraded by exonuclease. Plasmid loss may be minimized by using high specificity exonucleases or high efficiency conversion reactions or both.

In one embodiment, the exonuclease reaction may be performed using one or more single stranded DNA exonucleases, which preferentially degrade single stranded linear DNA versus double stranded linear DNA, such as exonuclease I. Thus, if some chromosomal DNA is in single stranded form, then such exonuclease reaction may reduce chromosomal DNA contamination. Experiments by the inventor suggest that some linear chromosomal DNA contamination from an alkaline lysis cleared lysate can be digested by exonuclease I. Optionally, double stranded linear chromosomal DNA could be converted to single stranded form by a brief denaturation step after the second reaction and prior to exonuclease digestion.

In another embodiment, the exonuclease reaction may be performed using one or more single stranded DNA exonucleases (which preferentially degrade single stranded linear DNA versus double stranded linear DNA) and one or more double stranded DNA exonucleases (which preferentially degrade double stranded linear DNA versus single stranded linear DNA). Preferably, at least one double stranded DNA exonuclease is a 5'-3' exonuclease. One advantageous combination comprises exonuclease I and T7 exonuclease. Another advantageous combination comprises exonuclease I and exonuclease III.

In another embodiment, one or more exonucleases is incubated concurrently with the conversion reactions (e.g. exonuclease I). After the second reaction, one or more additional exonucleases is then added to further digest chromosomal DNA (e.g. a double stranded DNA exonuclease).

In another embodiment, the exonuclease reaction may be performed using at least one 5'-3' double stranded DNA exonuclease (which preferentially degrades double stranded linear DNA versus single stranded linear DNA), such as T7 exonuclease.

In another embodiment, the exonuclease reaction may be performed using at least one high processivity exonuclease, such as exonuclease I.

In another embodiment, an exonuclease which has strong degrading activity on open circular plasmid could potentially be used concurrently with the conversion reactions. In this embodiment, the first and second reactions preferably occur rapidly to convert open circular plasmid to relaxed covalently closed circular plasmid in comparison to the exonuclease degradation of open circular plasmid, thereby minimizing loss of open circular plasmid. In this embodiment, there is an acceptable loss of open circular plasmid for the purpose of degrading linear chromosomal DNA. Preferably however, exonucleases which have strong degrading activity on open circular plasmid are not used during the first and second reactions.

Preferably, the exonuclease reaction is performed using at least one exonuclease which is not a DNA polymerase (or does not have DNA polymerase activity). Preferably, the exonuclease reaction is performed using at least one exonuclease which is not also a 3'-deblocking enzyme. The exonuclease reaction may be performed using sequential exonuclease incubations. Preferably however, the exonuclease reaction is performed using a single incubation.

Additional enzymes, such as PNKP or exonuclease III, may be useful in converting the termini of linear chromosomal DNA to the desired phosphorylation state to facilitate exonuclease digestion. Optionally, after a conversion reaction, plasmid may be purified prior to the exonuclease reaction. Preferably though, after the first reaction, plasmid is not purified prior to the exonuclease reaction.

The use of exonucleases for selective hydrolysis of chromosomal DNA in combination with conversion of open circular plasmid to supercoiled plasmid works synergistically to overcome the limitations of prior art uses of exonucleases. Prior exonuclease digestion methods for degrading chromosomal DNA fall into two categories. In one prior approach, exonucleases hydrolyze both chromosomal DNA and open circular plasmid. The disadvantage of this approach is that open circular plasmid is degraded. In the other prior approach, exonucleases hydrolyze only chromosomal DNA, leaving supercoiled and open circular plasmid intact. The disadvantage of this approach is that open circular plasmid must be removed by subsequent purification. The combination of exonuclease digestion of chromosomal DNA and conversion of open circular plasmid to supercoiled plasmid overcomes these disadvantages of the prior art. A single incubation could potentially produce high purity supercoiled plasmid with low levels of contaminating chromosomal DNA without significant loss of plasmid. The optional exonuclease reaction may be especially advantageous for low copy plasmids, which tend to have a higher percentage of chromosomal DNA contamination than high copy plasmids. The optional exonuclease reaction may be useful in combination with any method which converts open circular plasmid to supercoiled plasmid.

Optionally, a ribonuclease could be used to hydrolyze residual RNA. Ribonuclease incubation may be performed as a separate incubation or simultaneously with one or more conversion reactions. A preferred ribonuclease is ribonuclease I.

Optionally, undesired plasmid may be removed by selective restriction endonuclease digestion. If two or more plasmids are present in a plasmid solution, usually only one plasmid is the desired product. For example, a host cell may contain two different plasmids. Alternatively, two different plasmids could be generated from one plasmid by incubation with a recombinase. The resulting selectively linearized undesired plasmid could be further hydrolyzed by incubation with an exonuclease(s). It will be appreciated that the use of restriction enzyme in this manner does not involve degradation of the desired plasmid of interest.

In one embdiment, a change in reaction conditions (e.g. temperature, ionic strength, salt concentration, pH, buffer composition, presence/absence of additive) may be performed after the second reaction, so that at least one exonuclease used in the exonuclease reaction has increased activity in the changed conditions versus the reaction conditions of the second reaction. Preferably, the change in reaction conditions is performed after the third reaction. Preferably, the increase in activity is at least 50%, at least 100%, at least 200%, or at least 500%. This is illustrated in the following embodiments.

In one embodiment, a change in temperature may advantageously be used to change enzyme activity. For example, the conversion reactions may be performed at a lower temperature (e.g. 37° C.) using enzymes active at this lower temperature. After completing the conversion reactions, the temperature could be increased to a higher temperature (e.g. 60° C.) for selective degradation of chromosomal DNA, such as using thermophilic exonuclease(s), e.g. exonuclease I and/or III. At the higher temperature, the conversion enzymes are less active or inactive. At the lower temperature, the exonuclease(s) are less active or inactive, and thus do not interfere with the conversion reactions to an undesired extent. In a similar embodiment, a change in salt concentration may be used to change enzyme activity. The conversion reactions may be performed at a lower salt concentration using enzymes active at this lower salt concentration. After completing the conversion reactions, the salt concentration is increased for selective degradation of chromosomal DNA, such as using halophilic exonuclease(s). At the higher salt concentration, the conversion enzymes are less active or inactive. At the lower salt concentration, the exonuclease(s) are less active or inactive, and thus not do interfere with the conversion reactions to an undesired extent.

Catenation

DNA gyrase is known to reversibly catalyze the formation of catenanes (Kreutzer, Cell 20:245-254, 1980; Krasnow, J. Biol. Chem. 257:2687-2693, 1982). A catenane is formed by interlocking of two or more plasmid molecules, forming dimers or multimers. The formation of catenanes may be undesirable for gene transfer due to their larger molecular size. Preferably, the DNA gyrase incubation is performed to avoid or to minimize formation of catenanes. This may be accomplished by appropriate selection of buffer composition, such as the spermidine concentration or salt concentration, as taught in prior art. Potentially, the buffer composition could be selected such that the amount of catenanes in the plasmid solution would be reduced by the DNA gyrase incubation. Conversely, for applications in which catenanes are desirable, the buffer composition could be selected so that the amount of catenanes would be increased by the DNA gyrase incubation.

In the examples, no significant catenation was observed. At the highest plasmid concentration in Example 1 of 1.5 µg/µl, no significant catenation was observed. Based on visual inspection of agarose gels in the examples, it is estimated that the amount of catenane formation is less than approximately 1% to 5% of total plasmid. Preferably, the amount of catenane formation resulting from the third reaction is less than 1%, less than 5%, less than 10%, less than 15%, or less than 20% of the total plasmid; preferably, without the use of a potent decatenase.

If catenane formation does occur to an undesirable extent, then catenane formation could optionally be reduced by several possible methods. (1) The DNA gyrase reaction could be performed at a lower plasmid concentration or using a buffer composition that minimizes plasmid aggregation. (2) A DNA gyrase with stronger decatenase activity could be used, such as *Mycobacterum smegmatis* DNA gyrase. (3) An optional additional in vitro incubation with a potent decatenase enzyme, such as topoisomerase III or preferably topoisomerase IV, may be performed, whereby at least some catenanes, which may be present, are decatenated. The incubation with a potent decatenase is preferably performed simultaneously with the DNA gyrase reaction, but could be performed before or after the DNA gyrase reaction. Both potent decatenases are reported to relax supercoiled plasmid at a slow rate. Therefore, the potent decatenase is preferably used at a minimal concentration, to effect decatenation and to minimize supercoiled relaxation. Preferably, a purified form of the potent decatenase is used, such as chromatographically purified. In one embodiment, a potent decatenase incubation may be performed to reduce the amount of catenanes which may be present in a plasmid solution, preferably prior to the DNA gyrase reaction. In this embodiment, the potent decatenase may optionally be inactivated or removed prior to the DNA gyrase reaction. The nucleotide by-product of the potent decatenase nucleotide cofactor (usually ADP or analog) generated by the potent decatenase could be converted back to nucleotide cofactor (usually ATP or analog) as described earlier. Preferably though, incubation with a potent decatenase is not performed.

Plasmid Recovery

After the conversion reactions, the resulting plasmid may be used directly in some applications without further purification, so that recovery does not require additional steps. For other applications, after the conversion reactions, additional plasmid purification from the reaction solution may be desirable, for example to remove the buffer salts, or one or more of the enzymes, or nucleotides, or possibly exonuclease hydrolysis by-products. This may be accomplished by any method, such as organic solvent extraction, chromatography, precipitation, ultrafiltration, ultracentrifugation, electrophoresis, or combinations thereof. The additional purification may also remove residual open circular plasmid. The additional purification may also remove residual linear chromosomal DNA. The recovered supercoiled plasmid will usually be a mixture of supercoiled plasmid produced using the conversion reactions and supercoiled plasmid originally present in the cleared lysate.

In one advantageous embodiment, plasmid from a cleared lysate is purified chromatographically prior to the conversion reactions. After the conversion reactions, the plasmid product is purified chromatographically as a final "polishing" procedure. The preferred chromatographic method is anion exchange, before and after the conversion reactions. Commercially available anion exchange columns for plasmid purification may be useful (Qiagen, Macherey-Nagel). In one embodiment, the same chromatographic column is used before and after the conversion reactions, preferably an anion exchange column.

Applications for the recovered supercoiled plasmid may include transformation into recipient competent cells, such as tissue culture or whole animals, and especially for human therapeutic use. When the conversion reactions are used in combination with the optional exonuclease reaction, the final plasmid product may have a high percentage of supercoiled plasmid and a low percentage of chromosomal DNA contamination.

Optional Reuse of Enzyme

In one embodiment, one or more of the enzymes used in the conversion reactions or in the exonuclease reaction could be covalently attached to a solid support. The solid support-enzyme could be packed in a column, producing an immobilized enzyme column. An immobilized enzyme column could be made for each enzyme (or each conversion reaction) in the method separately; alternatively, a single immobilized enzyme column could contain a mixture of enzymes to convert unligatable open circular plasmid to supercoiled plasmid. Plasmid solution could be pumped through the column, or series of columns, converting unligatable open circular plasmid to supercoiled plasmid. Column eluate could be recycled through the column(s) as needed until a desired amount of the unligatable open circular plasmid is converted to supercoiled plasmid. An immobilized enzyme column could be used multiple times to prepare multiple plasmids with appropriate washing before reuse. Preferably, however, the enzymes are not attached to a solid support and are free in solution.

For bulk scale plasmid preparations, large quantities of enzymes may be needed. Optionally, it may be advantageous to recover one or more of the enzymes used in the conversion reactions or in the exonuclease reaction after the incubation so that the enzymes may be reused for subsequent plasmid preparations. To recover the enzyme(s), the enzyme(s) must be separated from the plasmid. This may be accomplished by using affinity chromatography (e.g. if the enzymes have an affinity tag) or classical chromatography (e.g. anion or cation exchange or dye ligand). Loss of enzyme activity during incubation is preferably minimized. This may be accomplished by lowering the incubation temperature or by adding stabilizers of enzyme activity, such as glycerol, Triton X-100, spermidine, or dithiothreitol.

In one advantageous embodiment, one or more enzymes used in the conversion reactions or in the exonuclease reaction may be thermophilic and derived from a thermophilic organism. A thermophilic enzyme is an enzyme with optimal activity at a temperature of about 50 degrees C. or higher. For example, some or all of the enzymes could be derived from a thermophilic prokaryote, such as *Bacillus stearothermophilus*, or a thermophilic eukaryote, such as *Thermomyces lanuginosus*. The incubation(s) with thermophilic enzyme(s) could be performed at temperatures between about 45° C. and 75° C. Thermophilic enzymes would likely maintain most of their activity during the incubation, optionally allowing reuse for subsequent incubations if desired.

Miscellaneous Aspects

Most plasmid preparations contain a mixture of supercoiled and open circular plasmid prior to the conversion reactions. After preparing a cleared lysate, it is preferable to preserve the supercoiled plasmid prior to and during the conversion reactions. Therefore, additional reactions which work against this objective are preferably not performed. After preparing a cleared lysate, the conversion reactions are preferably performed without prior purposeful in vitro conversion of supercoiled plasmid to an undesired form. Undesired forms include linear, open circular, relaxed covalently closed circular, replicated daughter plasmids (partial or complete), single stranded circular, triple stranded, single-strand invasion, or Holliday structure forms.

It will be appreciated that other methods with different ultimate goals may include additional steps that are appropriate for achieving the goals of those methods, but that are not required to achieve the goals of the presently claimed methods. However, in some cases, the processing that is carried out by the recited steps of these present method may may at least partially achieve the result of the steps of another method. As used in the specification and claims of this application, the term "purposefully" as used to describe a step that is excluded refers to separate steps undertaken to achieve a specific recited purpose, and does not exclude incidental occurrence of the result through the processing steps recited or de minimus modification solely for the purpose of avoiding infringement without changing the ultimate intent and goal of the method.

After preparing a cleared lysate, it is preferable to preserve the open circular plasmid so that it may be quantitatively converted to supercoiled plasmid. Therefore, additional reactions which work against this objective are preferably not performed. After preparing a cleared lysate, the first and second reactions are preferably performed without prior purposeful in vitro conversion of open circular plasmid to an undesired form. Undesired forms include linear, single stranded circular, triple stranded, single-strand invasion, in vitro replicated daughter plasmids (partial or complete), Holliday structure forms, or forms with impaired ability to be subsequently converted to covalently closed circular plasmid. After preparing the cleared lysate, the first and second reactions are preferably performed without prior purposeful separation of supercoiled plasmid from the open circular plasmid.

In some embodiments, some open circular plasmid may be separated from supercoiled plasmid prior to the first reaction. Preferably in such embodiments however, less than 5%, less than 10%, or less than 20% of open circular plasmid is separated from supercoiled plasmid prior to the first reaction.

The following embodiments may be especially advantageous. After preparing a cleared lysate, the cleared lysate usually comprises supercoiled plasmid in addition to open circular plasmid. After preparing a cleared lysate, the supercoiled plasmid is preferably not purposefully modified prior to the first reaction. Purposeful modification is usually a quantitative conversion, in which most of the material is converted to a different form. Preferably, after preparing a cleared lysate and prior to the first reaction, supercoiled plasmid from the cleared lysate is not purposefully converted to open circular form, for example by intentional free radical nicking. Preferably, after preparing a cleared lysate and prior to the first reaction, supercoiled plasmid is not purposefully converted to relaxed covalently closed circular plasmid, for example by intentional incubation with topoisomerase I. Preferably, after preparing a cleared lysate and prior to the first reaction, supercoiled plasmid (or open circular plasmid) is not purposefully converted to linear form, for example by restriction digestion. Preferably, after preparing a cleared lysate and prior to the first reaction, open circular plasmid in the plasmid solution is not purposefully converted to single stranded circular DNA, for example by heat or alkali. Preferably, after preparing a cleared lysate, and prior to the first reaction, open circular plasmid is not purposefully separated from supercoiled plasmid.

Preferably, the first reaction is performed without purposeful in vitro plasmid replication. More preferably, the conversion reactions are performed without purposeful in vitro plasmid replication and without prior purposeful in vitro plasmid replication. "In vitro plasmid replication" is defined herein as enzymatic production of daughter plasmid molecules (either partial or complete synthesis) from a parent plasmid in vitro. Partial production of daughter molecules on some plasmids begins with initiation of new strand synthesis and produces a theta structure as viewed with an electron microscope. Partial production of daughter molecules by rolling circle replication results in production of single stranded molecules from the parent plasmid. It will be appreciated that in the first reaction, DNA polymerase may generate a small amount of displaced single stranded DNA by strand displacement as an unintentional side reaction of DNA repair of open circular plasmid, not as intentional plasmid replication. Such flaps may potentially be repaired using a flap endonuclease. Examples of in vitro plasmid replication are described by Funnel et al. (J. Biol. Chem. 261:5616-5624, 1986) and Hiasa et al. (J. Biol. Chem. 269:2093-2099, 1994). Preferably, in vitro plasmid replication is not performed after the conversion reactions. The method of the present invention is a method for converting plasmid from an open circular plasmid to supercoiled plasmid. The intention of the invention is not to produce daughter plasmid through a process of in vitro replication. Although some replication may occur as a result of incidental or contaminating enzyme activity, there is no "purposeful replication". In the specification and claims of this invention, the term "purposeful replication" encompasses the addition of enzyme(s) (e.g. primases, etc) that are added intentionally for the purpose of bringing about plasmid replication.

Preferably, the first reaction is performed without significant plasmid in vitro displacement loop formation or in vitro plasmid theta structure formation. More preferably, the conversion reactions are performed without significant plasmid in vitro displacement loop formation, without in vitro plasmid theta structure formation, and without prior such in vitro formation of either (Kornberg, DNA replication, second edition, 1992, especially FIG. 16-1).

Preferably, after preparing a cleared lysate and prior to the first reaction, the nucleotide sequence of the plasmid is not modified.

Preferably, the conversion reactions are performed without an in vitro incubation, or prior in vitro incubation, with a primase enzyme or an RNA polymerase enzyme, which may produce primers for synthesis of daughter strands of plasmid. Preferably, the conversion reactions are performed without in vitro incubation, or prior in vitro incubation, with any combination of one or more of DnaA, DnaB, DnaC, and DnaG proteins. Preferably, the first reaction is performed without purposeful in vitro synthesis of RNA using plasmid template, e.g. using a primase or RNA polymerase enzyme. More preferably, the conversion reactions are performed without purposeful in vitro synthesis of RNA using plasmid template, and without prior such in vitro synthesis.

In some embodiments, the plasmid solution may further comprise purposefully in vitro synthesized open circular plasmid prior to the first reaction. Preferably however, the plasmid solution does not comprise purposefully in vitro synthesized open circular plasmid prior to the first reaction. Preferably, the conversion reactions are performed without purposeful in vitro synthesis of open circular plasmid, for example from nucleic acid which is not open circular plasmid.

Preferably, the conversion reactions are performed without significantly increasing the total amount of plasmid in vitro, where any increase in the amount of plasmid by conversion of open circular to closed circular plasmid is not considered significant. Preferably, the conversion reactions are performed without a prior in vitro reaction which increases the total amount of plasmid. Preferably, the conversion reactions are performed without significantly increasing in vitro the total number of plasmid molecules. Preferably, the conversion reactions are performed with a prior in vitro reaction which increases the total number of plasmid molecules. In some embodiments, the conversion reactions may be performed so that the total amount of plasmid is substantially unchanged. In other embodiments, a substantial amount of plasmid may be lost, such as potentially in the optional exonuclease reaction.

Preferably, the conversion reactions are performed without significantly increasing the total amount (mass) of plasmid derived DNA. However, in some embodiments, an additional in vitro enzymatic reaction may be performed which results in an increase in the total amount of plasmid derived DNA. Plasmid derived DNA is plasmid and DNA, in any form (e.g. single stranded, double stranded, triple stranded, etc, which may or may not be covalently attached or annealed to plasmid), synthesized by a template dependent DNA polymerase using plasmid as the template. Preferably, the conversion reactions are performed without performing an additional in vitro enzymatic reaction which increases the total amount of plasmid derived DNA by greater than 5%, greater than 10%, or greater than 20%. An example of such an in vitro enzymatic reaction is in vitro plasmid replication.

Preferably, the conversion reactions are performed so that the amount of supercoiled plasmid after the conversion reactions is increased from the starting amount of supercoiled plasmid in the plasmid solution immediately prior to the conversion reactions. Preferably, this is accomplished without increasing the total amount of plasmid.

Preferably, the conversion reactions are performed so that the percentage of plasmid which is supercoiled plasmid after the conversion reactions is increased from the starting percentage of plasmid which is supercoiled plasmid in the plasmid solution immediately prior to the conversion reactions.

Preferably, this is accomplished without separation of open circular plasmid from supercoiled plasmid prior to completing the second reaction.

Preferably, the conversion reactions are performed in a manner to minimize or avoid in vitro recombination events. For example, the conversion reactions are preferably performed substantially in the absence of RecA protein or substantially in the absence of single stranded DNA binding protein. Preferably, the conversion reactions are performed without purposeful conversion of plasmid to triple stranded forms, Holliday structures, or other strand invasion forms, and/or without prior such in vitro conversion.

Preferably, the conversion reactions are performed using purified enzymes. This can be accomplished for example by using chromatographic purification. Preferably, the convresion enzymes are produced as recombinant enzymes. Preferably, the conversion reactions are not performed using a crude extract as a source of enzyme, such as a cell lysate. However, an unpurified lysate could potentially be used for one or more of the enzymes, for example, if the enzyme is a large fraction of the unpurified lysate. A purified form of an enzyme, produced from producer cells, is obtained by a process which removes at least some, or preferably at least 5%, at least 10%, at least 25%, at least 50%, or at least 75% of producer cell protein which is not the enzyme. Preferably, the percent purity of a purified form of an enzyme is at least 5%, at least 10%, at least 25%, at least 50%, or at least 75% of total protein by weight, excluding any protein additives which may be added subsequent to purification. It will be appreciated that after purification of an enzyme, protein stabilizers such as albumin may be added to the purified enzyme preparation. Preferably, a purified form of an enzyme is obtained by a process which removes most or substantially all of the producer cell chromosomal DNA.

Preferably, at least one enzyme used in the conversion reactions is added exogenously to the plasmid solution. More preferably, DNA polymerase, DNA ligase, and DNA gyrase are added exogenously to the plasmid solution. More preferably, the latter enzymes are purified enzymes.

Modified nucleotide(s) or dNTP analog(s) may be used in the first reaction using DNA polymerase. The use of labeled nucleotides may be advantageous in producing labeled supercoiled plasmid. In one embodiment, at least one labeled nucleotide may be used in the first reaction with DNA polymerase, so that at least some open circular plasmid is converted to labeled supercoiled plasmid in the conversion reactions. In another embodiment, (i) supercoiled plasmid in the plasmid solution is purposefully converted to in vitro synthesized open circular plasmid, either prior to or during the first reaction; and (ii) at least one labeled nucleotide is used in the first reaction with DNA polymerase, so that at least some open circular plasmid and some in vitro synthesized open circular plasmid is converted to labeled supercoiled plasmid. Preferably however, the first reaction using DNA polymerase is performed substantially in the absence of labeled nucleotide(s). Preferably, the conversion reactions are performed without incorporating modified nucleotide analog(s) into the plasmid. Preferably, the first reaction using DNA polymerase is performed substantially without incorporating deoxyribose moiety modified nucleotide analog(s) into the plasmid. Preferably, the first reaction using DNA polymerase is performed substantially without incorporating phosphate moiety modified nucleotide analog(s) into the plasmid.

Preferably, the conversion reactions are performed at a total plasmid concentration between about 0.1 μg/μl to about 10 μg/μl, or more preferably between about 0.2 μg/μl to about 5.0 μg/μl. Preferably, the total mass of the enzymes used in the conversion reactions represents at least 10%, at least 25%, at least 50%, or at least 75% of the total protein in the conversion reactions.

Preferably, the open circular plasmid in the plasmid solution prior to the first reaction consists of (i) open circular plasmid which existed in host cells immediately prior to lysis, or (ii) supercoiled plasmid in host cells which was unintentionally converted to open circular plasmid in the preparation of the cleared lysate, or (iii) supercoiled plasmid in the cleared lysate which was unintentionally converted to open circular plasmid after further plasmid purification from other host cell components, or (iv) combination thereof. Unintentional conversion is the consequence of the inherent instability of supercoiled plasmid to DNA damage. Preferably, essentially all of the plasmid in the plasmid solution was synthesized by the host cells.

It will be appreciated that unintentional plasmid modification may occur. This may result from enzyme impurities. For example, nuclease contamination may convert some supercoiled plasmid to open circular plasmid. Unintentional conversion may also result from the side reactions due to inherent activities of the enzymes used. Several examples illustrate this point. (1) The optional exonuclease reaction may hydrolyze some plasmid due to lack of absolute substrate selectivity. This loss is not considered purposeful, since the purpose of the exonuclease reaction is degradation of chromosomal DNA and/or degradation of remaining open circular plasmid after the second reaction. (2) AP endonuclease may convert some supercoiled plasmid to open circular plasmid, if the supercoiled plasmid contains an abasic site. This conversion is not considered purposeful, since the purpose of the AP endonuclease is the repair of open circular plasmid.

Enzyme Reagents

Performing the conversion reactions is facilitated by using premixed enzyme reagents. A preferred enzyme composition comprises DNA polymerase, DNA ligase, and DNA gyrase. The preferred composition may further comprise one or more 3' deblocking enzymes. The preferred composition may further comprise one or more 5' deblocking enzymes. A preferred enzyme composition for the alternate mode comprises polynucleotide kinase, 3'-phosphatase, DNA ligase, and DNA gyrase. Another useful enzyme composition comprises DNA gyrase and exonuclease(s).

The above enzyme compositions may further comprise one or more of the following enzymes: (1) kinase enzyme to regenerate nucleotide cofactor, (2) one or more exonucleases to hydrolyze residual chromosomal DNA, (3) inorganic pyrophosphatase, (4) ribonuclease, and (5) potent decatenase (preferably topoisomerase IV).

Preferably, the enzyme composition does not further comprise additional enzymes which result in (i) in vitro plasmid replication and (ii) in vitro conversion of single stranded circular DNA to open circular form without using a synthetic primer. Preferably, the enzyme composition does not further comprise primase or RNA polymerase Preferably, the enzyme composition does not further comprise single stranded DNA binding protein. Preferably, the enzyme composition does not further comprise substantial topoisomerase I contamination. Preferably, the enzyme composition does not further comprise DnaA, DnaB, DnaC, or DnaG protein. Preferably, at least one exonuclease in a kit or composition is not a DNA polymerase. Preferably, at least one exonuclease in a kit or composition is not also a 3'-deblocking enzyme. Preferably, the total mass of the enzymes recited in the composition represent at least 10%, at least 25%, at least 50%, or at least 75% of the total protein in the composition.

A purified form of at least one of said enzymes is used to make the above compositions, such as chromatographically purified. Preferably, a purified form of all of said enzymes is used to make the above compositions, such as chromatographically purified. The enzymes of the composition could be produced using recombinant DNA technology as genetic fusions with affinity fusion protein tags, such as polyhistidine, to facilitate purification by chromatography. The enzymes could be purified to decrease endotoxin contamination to low levels. The enzyme reagents could be supplied in dry lyophilized form, or as an aqueous solution (e.g. buffered 50% glycerol solution).

Advantages over Prior Art

The present invention offers three potential fundamental advantages over prior art methods: (1) increased yield of supercoiled plasmid, (2) uniformly highly supercoiled state, and (3) one universal procedure for all plasmids. These advantages are discussed further.

The above methods differ in a fundamental manner from prior art methods for purifying supercoiled plasmid. Prior art methods are based on excluding open circular plasmid from the final plasmid preparation. The invention is based on including a converted form of open circular plasmid in the final plasmid preparation, by enzymatically converting open circular plasmid to supercoiled plasmid. Surprisingly and unexpectedly, using a preferred mode of the first reaction, nearly all of the open circular plasmid can be converted to supercoiled plasmid.

As a consequence of the inclusion principle, one potential advantage over prior art methods is increased supercoiled plasmid yield. In some embodiments, the inventor has observed substantially no loss of plasmid in the conversion reactions. This is illustrated in Examples 1 and 2. In contrast, prior art methods are based on separation, which involves loss of plasmid. In prior art methods, the open circular plasmid is lost during the separation process. In addition, some supercoiled plasmid is also lost in any prior art separation process due to imperfect resolution of separation.

As a result of this advantage, there is less concern about loss of supercoiled plasmid due to damage which converts it to open circular form (e.g. during the fermentation, producing cleared lysate, or further purifying the plasmid to create the plasmid solution), because open circular plasmid is converted to supercoiled plasmid. This method may be especially useful for large plasmids, which tend to have a higher percentage of open circular plasmid due to the greater fragility of large plasmids. This method may be especially useful for bulk scale plasmid preparations, which tend to have a higher percentage of open circular plasmid due to longer processing times.

In addition, the above methods provide a potential solution to a previously unrecognized problem in the art of plasmid preparation—the extent of supercoiling. The extent of supercoiling of plasmid can vary from batch to batch and under different host cell growth conditions. The extent of supercoiling may have an effect on the biological activity of the plasmid. For example, a plasmid preparation which has a low extent of supercoiling may be less bioactive than desired. The extent of supercoiling of plasmid in bacteria is not at its thermodynamic maximum (Cullis et al., Biochemistry 31:9642-9646, 1992). This is due to topoisomerase I which relaxes supercoiled plasmid in the bacterial host. The extent of supercoiling in vivo is an equilibrium effect between DNA gyrase and topoisomerase I. Occasionally, the extent of supercoiling in a host may be far below normal or a plasmid solution may contain a large amount of relaxed covalently closed circular plasmid. This poorly supercoiled plasmid could occur during the fermentation of host cells, possibly due to nutrient starvation, cell death, low ATP energy charge, or other effect.

This previously unrecognized problem may be solved by DNA gyrase incubation in the third reaction. The DNA gyrase incubation could increase the extent of supercoiling to its maximum thermodynamic limit or close to this limit. The increased supercoiling of the plasmid could create a more condensed molecule with potentially greater transformability. The DNA gyrase incubation could convert plasmid (including supercoiled plasmid from the cleared lysate) to a more uniformly highly supercoiled and condensed state. To the inventor's knowledge, the use of DNA gyrase in the art of plasmid preparation to solve this previously unrecognized problem has not been reported. The inventor has confirmed experimentally that the DNA gyrase incubation is able to increase the extent of supercoiling of poorly supercoiled plasmid in a plasmid solution.

Surprisingly and unexpectedly, the inventor believes that a universal procedure in accordance with the invention could potentially work well for nearly all plasmids. Enzyme concentrations and incubation times may be the same for nearly all plasmids, providing suitable conversion efficiency, regardless of plasmid size, plasmid GC content, plasmid DNA sequence, percent supercoiled plasmid in the plasmid solution, and percent of chromosomal DNA contamination. In other words, the details of the procedure (such as enzyme concentrations and incubation times) would likely not need to be optimized for each individual plasmid. A single universal procedure may work well for nearly all plasmids, providing suitable conversion efficiency. In contrast, prior art methods usually require optimization for each individual plasmid, in order to maximize the separation of supercoiled from open circular plasmid, while minimizing loss of supercoiled plasmid. For example, chromatographic purification of supercoiled plasmid usually requires optimization of the gradient and sample load amount for each individual plasmid.

A further advantage may be to ensure consistent and reproducible proportions of supercoiled plasmid in the final plasmid preparation, reducing batch to batch variation.

To the inventor's knowledge, DNA gyrase, DNA ligase, DNA polymerase, polynucleotide kinase, and 3'-phosphatase have never been applied in the field of plasmid purification. The use of these enzymes breaks new ground in the art of plasmid preparation.

Several different embodiments of the invention are demonstrated in the following non-limiting examples.

Materials and Methods

Purified enzymes were obtained as follows. T4 DNA ligase and human PNKP were produced as fusion proteins with glutathione-S-transferase (GST) affinity tag as follows. The genes coding for these enzymes were amplified by the polymerase chain reaction. The genes were cloned into pGEX, a commercially available expression vector (Amersham) so that the GST affinity tag was fused to the amino terminus of the enzyme. The fusion proteins were purified on glutathione-agarose according to the manufacturer's instructions. These fusion proteins are denoted GST-T4 DNA ligase and GST-PNKP. *E. coli* DNA gyrase was obtained from John Innes Ltd. *E. coli* DNA polymerase I, phage T4 DNA polymerase, phage lambda exonuclease, phage T7 exonuclease (gene 6), *E. coli* exonuclease I, and *E. coli* exonuclease III were obtained from New England Biolabs. *E. coli* endonuclease IV was obtained from Epicentre. *M. luteus* exonuclease V was obtained from USB Corp. Enzyme concentrations were not necessarily optimized in the following examples. For instance, the first part of Example 1 was repeated using one-tenth the amount of GST-T4 DNA ligase with substantially the same result.

A four kilobase plasmid in an *E. coli* host was prepared using the alkaline lysis method, followed by further purification to remove RNA and protein. Agarose gel electrophoresis showed approximately 30% open circular plasmid, 70% supercoiled plasmid, and some residual chromosomal DNA was likely present. This plasmid preparation, denoted p4kb, was used in the subsequent examples. A 10-kilobase plasmid, denoted p10kb, was prepared in the same manner, comprising approximately 50% open circular plasmid and 50% supercoiled plasmid.

EXAMPLE 1

Preferred Mode

A 10 μl reaction volume contained 5 μg p4kb plasmid, 35 mM Tris-HCl (pH 7.5), 25 mM KCl, 4 mM $MgCl_2$, 2 mM dithiothreitol, 1.8 mM spermidine, 1 mM ATP, 6.4% glycerol, 0.1 mg/ml bovine serum albumin, 2.5 units DNA gyrase, 2.8 μg GST-T4 DNA ligase, 0.2 units DNA polymerase I, 200 μM dATP, 200 μM dGTP, 200 μM dCTP, and 200 μM dTTP. This reaction was incubated at 37° C. for 2 hours. After incubation, the plasmid was analyzed by agarose gel electrophoresis. The gel showed a high yield of supercoiled plasmid, confirming conversion of most of the open circular plasmid to supercoiled plasmid. By visual inspection of the stained gel, it is estimated that about 80% to 85% of open circular plasmid was converted to supercoiled form. Based on flourometry analysis, the total amount of plasmid measured before and after the reaction was the same. Extending the incubation time to 4 hours resulted in about 95% conversion. A 2-hour incubation using 1 μg p4kb resulted in about 95% conversion. A 4-hour incubation using 15 μg p4kb resulted in about 85% conversion. A 2-hour incubation using 5 μg p10kb resulted in about 80-85% conversion. A 2-hour incubation using 5 μg p4kb and 0.2 units T4 DNA polymerase (instead of DNA polymerase I) resulted in about 40% conversion. As a control, a 2-hour incubation using 5 μg p4kb and only the enzymes GST-T4 DNA ligase and DNA gyrase resulted in only about 5% conversion.

EXAMPLE 2

Preferred Mode+3' Deblocking Enzyme

A 10 μl reaction volume contained 5 μg p4kb plasmid, 35 mM Tris-HCl (pH 7.5), 25 mM KCl, 4 mM $MgCl_2$, 2 mM dithiothreitol, 1.8 mM spermidine, 1 mM ATP, 6.4% glycerol, 0.1 mg/ml bovine serum albumin, 2.5 units DNA gyrase, 2.8 μg GST-T4 DNA ligase, 0.2 units DNA polymerase I, 200 μM dATP, 200 μM dGTP, 200 μM dCTP, 200 μM dTTP, and 0.5 units exonuclease III. This reaction was incubated at 37° C. for 2 hours. After incubation, the plasmid was analyzed by agarose gel electrophoresis. The gel showed high purity supercoiled plasmid, confirming conversion of virtually all of the open circular plasmid to supercoiled plasmid. The open circular band was barely visible on the gel. By visual inspection of the stained gel, it is estimated that greater than about 95% to 99% of open circular plasmid was converted to supercoiled form. Based on flourometry, the total amount of plasmid measured before and after the reaction was the same. A 4-hour incubation using 15 μg p4kb resulted in greater than 95% conversion. A 2-hour incubation using 5 μg p10kb resulted in about 95% conversion. A 2-hour incubation using 5 μg p4kb and 1 unit endonuclease IV (instead of exonuclease III) resulted in greater than about 95% to 99% conversion. A 2-hour incubation using 5 μg p4kb and 1.4 μg GST-PNKP (instead of exonuclease III) resulted in about 90% to 95% conversion.

EXAMPLE 3

Preferred Mode+ATP Regeneration

A 10 μl reaction volume contained 5 μg p4kb plasmid, 35 mM Tris-HCl (pH 7.5), 25 mM KCl, 4 mM $MgCl_2$, 2 mM dithiothreitol, 1.8 mM spermidine, 1 mM ATP, 6.4% glycerol, 0.1 mg/ml bovine serum albumin, 2.5 units DNA gyrase, 2.8 μg GST-T4 DNA ligase, 0.2 units DNA polymerase I, 200 μM dATP, 200 μM dGTP, 200 μM dCTP, 200 μM dTTP, 0.05 units creatine kinase (Sigma C3755), and 1 mM creatine phosphate. This reaction was incubated at 37° C. for 2 hours. After incubation, the plasmid was analyzed by agarose gel electrophoresis. The gel showed high purity supercoiled plasmid, confirming conversion of most of the open circular plasmid to supercoiled plasmid. By visual inspection of the stained gel, it is estimated that about 75% to 80% of open circular plasmid was converted to supercoiled form.

EXAMPLE 4

Preferred Mode+Concurrent Exonuclease Digestion

A 10 μl reaction volume contained 5 μg p4kb plasmid, 35 mM Tris-HCl (pH 7.5), 25 mM KCl, 4 mM $MgCl_2$, 2 mM dithiothreitol, 1.8 mM spermidine, 1 mM ATP, 6.4% glycerol, 2.5 units DNA gyrase, 2.8 μg GST-T4 DNA ligase, 0.2 units DNA polymerase I, 200 μM dATP, 200 μM dGTP, 200 μM dCTP, 200 μM dTTP, and 0.5 units exonuclease V. This reaction was incubated at 37° C. for 2 hours. After the incubation, the plasmid was analyzed by agarose gel electrophoresis. The gel showed high purity supercoiled plasmid, confirming conversion of most of the open circular plasmid to supercoiled plasmid. By visual inspection of the stained gel, it is estimated that about 80% to 85% of open circular plasmid was converted to supercoiled form.

A 2-hour incubation using 1 unit lambda exonuclease and 5 units exonuclease I (instead of exonuclease V) resulted in about 80% to 85% conversion. Based on flourometry, in the latter experiment, the loss of DNA in the enzymatic reaction was about 3%. This DNA loss is likely a loss of some chromosomal DNA and possibly a loss of a small amount of plasmid. In separate experiments, the inventor has determined that lambda exonuclease is able to degrade a small amount of open circular plasmid, due to lack of absolute substrate specificity for linear DNA. Based on the stained agarose gel, this plasmid preparation contained slightly less open circular plasmid than the same incubation performed without the exonucleases.

EXAMPLE 5

Preferred Mode+Subsequent Exonuclease Digestion

A 20 μl reaction volume contained 5 μg p4kb plasmid, 35 mM Tris-HCl (pH 7.5), 25 mM KCl, 4 mM $MgCl_2$, 2 mM dithiothreitol, 1.8 mM spermidine, 1 mM ATP, 6.4% glycerol, 2.5 units DNA gyrase, 2.8 μg GST-T4 DNA ligase, 0.2 units DNA polymerase I, 200 μM DATP, 200 μM dGTP, 200 μM dCTP, and 200 μM dTTP. This reaction was incubated at 37° C. for 2 hours. After this conversion reaction incubation, the following exonucleases were subsequently added: 0.5 μl 20 units/μl exonuclease I, 1.0 μl 10 units/μl T7 exonuclease, and 1.0 μl 1.0 units/μl exonuclease III. The reaction was incubated an additional 2 hours at 37° C. After incubation, the plasmid was analyzed by agarose gel electrophoresis. The stained gel showed only supercoiled plasmid, with no visible open circular plasmid. Based on flourometry, the loss of DNA in the subsequent exonuclease incubation was about 12%. This DNA loss is likely a loss of both linear chromosomal DNA and residual open circular plasmid. This residual open circular plasmid, remaining after the conversion reactions, is subsequently degraded by both exonuclease III and T7 exonuclease. Separate experiments by the inventor suggest that this exonuciease mixture, used at this concentration and duration, may reduce linear chromosomal DNA contamination by 50 fold. Based on visual inspection of the stained gel, no significant degradation of supercoiled plasmid was observed by this subsequent exonuclease incubation.

EXAMPLE 6

Alternate Mode

A 10 μl reaction volume contained 5 μg p4kb plasmid, 35 mM Tris-HCl (pH 7.5), 25 mM KCl, 4 mM $MgCl_2$, 2 mM dithiothreitol, 1.8 mM spermidine, 1 mM ATP, 6.4% glycerol, 0.1 mg/ml bovine serum albumin, 2.5 units DNA gyrase, 2.8 μg GST-T4 DNA ligase, and 1.4 μg GST-PNKP. This reaction was incubated at 37° C. for 2 hours. After incubation, the plasmid was analyzed by agarose gel electrophoresis. The gel showed conversion of a small amount of the open circular plasmid to supercoiled plasmid. Conversion of some open circular plasmid to supercoiled form was confirmed using purified open circular p4kb. Based on flourometry, the total amount of plasmid measured before and after the reaction was the same.

Patents, patent applications, books, and other publications cited herein are incorporated by reference in their entirety. All modifications and substitutions that come within the meaning of the claims and the range of their legal equivalents are to be embraced within their scope.

I claim:

1. A method for preparing negatively supercoiled plasmid from unligatable open circular plasmid, the method comprising:
   (a) providing a plasmid solution from host cells containing plasmid, wherein the plasmid solution comprises unligatable open circular plasmid;
   (b) reacting in vitro the plasmid solution of (a) with one or more enzymes, such that at least some unligatable open circular plasmid in the plasmid solution is converted to 3'-hydroxyl, 5'-phosphate nicked plasmid;
   (c) reacting in vitro the 3'-hydroxyl, 5'-phosphate nicked plasmid with a DNA ligase, such that at least some 3'-hydroxyl, 5'-phosphate nicked plasmid is converted to relaxed covalently closed circular plasmid; and
   (d) reacting in vitro the relaxed covalently closed circular plasmid with a DNA gyrase, such that at least some relaxed covalently closed circular plasmid is converted to negatively supercoiled plasmid; and wherein at least one of the enzymes used in reactions (b), (c) or (d) is a purified form of the enzyme.

2. The method according to claim 1, wherein reaction (b) is performed with a DNA polymerase.

3. The method according to claim 2, wherein reaction (b) is performed with a DNA polymerase, and optionally a 3' deblocking enzyme, and optionally a 5' deblocking enzyme, and wherein at least one repair activity is provided for the 3' terminus of open circular plasmid and at least one repair activity is provided for the 5' terminus of open circular plasmid.

4. The method according to claim 2, wherein the DNA polymerase has both 3'-5' and 5'-3' exonuclease activities.

5. The method according to claim 2, wherein reactions (b), (c), and (d) are combined in a single in vitro incubation, by incubating with a mixture comprising a DNA polymerase, a DNA ligase, and a DNA gyrase.

6. The method according to claim 5, wherein the plasmid solution further comprises linear chromosomal DNA and the mixture further comprises an exonuclease which is not a DNA polymerase and not a 3'-deblocking enzyme, whereby at least some linear chromosomal DNA is degraded.

7. The method according to claim 1, wherein reaction (d) is performed with a DNA gyrase in the presence of DNA gyrase cofactor, and wherein reaction (d) is performed in the presence of a kinase enzyme, whereby said kinase enzyme converts the nucleotide by-product of DNA gyrase nucleotide cofactor back to nucleotide cofactor.

8. The method according to claim 1, wherein reaction (b) is performed with a 3' deblocking enzyme and DNA polymerase.

9. The method according to claim 8, wherein reactions (b), (c), and (d) are combined in a single in vitro incubation, by incubating with a mixture comprising a 3' deblocking enzyme, DNA polymerase, DNA ligase, and DNA gyrase.

10. The method according to claim 8, wherein the 3' deblocking enzyme is selected from the group consisting of exonuclease III, an enzyme with apurinic/apyrimidinic endonuclease activity, 3'-phosphatase, polynucleotide kinase-3'-phosphatase, and combinations thereof.

11. The method according to claim 1, wherein the plasmid solution further comprises linear chromosomal DNA and the method further comprises (e) reacting in vitro the linear chromosomal DNA with one or more exonucleases, whereby at least some linear chromosomal DNA is degraded.

12. The method according to claim 11, wherein at least one of the exonuclease(s) is exonuclease I, exonuclease III, exonuclease V, exonuclease VII, exonuclease VIII, lambda exonuclease, T5 exonuclease, T7 exonuclease, the 3'-5' exonuclease of DNA polymerase, or RecJf.

13. The method according to claim 11, wherein the exonuclease reaction is performed using at least one single stranded DNA exonuclease and at least one double stranded DNA exonuclease.

14. The method according to claim 11, wherein at least 75% of the linear chromosomal DNA is degraded.

15. The method according to claim 11, wherein at least one of the exonucleases used in reaction (e) is a purified form of the exonuclease.

16. The method according to claim 11, wherein reaction (b) is performed with a purified DNA polymerase, reaction (c) is performed with a purified DNA ligase, and reaction (d) is performed with a purified DNA gyrase.

17. The method according to claim 1, wherein at least one of said enzymes of (b), (c), or (d) is a chromatographically purified form of said enzyme.

18. The method according to claim 1, wherein (a) is performed by preparing a cleared lysate of the host cells, and optionally further purifying plasmid from other host cell components, resulting in a plasmid solution comprising open circular plasmid.

19. The method according to claim 18, wherein the cleared lysate comprises supercoiled plasmid and open circular plasmid, and wherein the open circular plasmid is not separated from supercoiled plasmid after preparing the cleared lysate and prior to reaction (b).

20. The method according to claim 18, wherein the cleared lysate is obtained by a method comprising (i) lysing the host cells, thereby releasing plasmid and chromosomal DNA into a lysate solution; (ii) precipitating the chromosomal DNA from the lysate solution; and (iii) removing the precipitated chromosomal DNA and cell debris from the lysate solution; resulting in a cleared lysate.

21. The method according to claim 18, wherein open circular plasmid in the plasmid solution prior to reaction (b) consists essentially of: (i) open circular plasmid which was present in the host cells prior to cell lysis, or (ii) supercoiled plasmid in the host cells which was unintentionally converted to open circular plasmid during preparation of the cleared lysate, or (iii) supercoiled plasmid in the cleared lysate which was unintentionally converted to open circular plasmid by further purification of plasmid from other host cell components, or (iv) a combination thereof.

22. The method according to claim 1, wherein the plasmid solution is obtained by a process which separates host cell chromosomal DNA from plasmid.

23. The method according to claim 1, wherein the host cells are bacterial cells.

24. The method according to claim 1, wherein reaction (d) results in less than 20% of total plasmid in catenated form.

25. The method according to claim 1, further comprising (e) reacting catenanes, which may be present, in vitro with a potent decatenase, whereby at least some catenanes are decatenated.

26. The method according to claim 1, wherein greater than 75% of open circular plasmid in the plasmid solution is converted to negatively supercoiled plasmid by reactions (b), (c), and (d).

27. The method according to claim 1, wherein reaction (b) is performed with 3'-phosphatase and polynucleotide kinase.

28. The method according to claim 1, wherein the plasmid solution obtained from processing the host cells further comprises supercoiled plasmid and wherein reactions (b), (c), and (d) are performed (i) without prior purposeful in vitro conversion of the supercoiled plasmid to linear form, (ii) without prior purposeful in vitro conversion of the supercoiled plasmid to open circular form, (iii) without prior purposeful in vitro conversion of the supercoiled plasmid to relaxed covalently closed circular plasmid; and wherein reactions (b) and (c) are performed without prior purposeful in vitro conversion of open circular plasmid of (a) to single stranded circular DNA.

29. The method according to claim 1, wherein reactions (b), (c), and (d) are performed without purposeful in vitro plasmid replication and without prior purposeful in vitro plasmid replication.

30. The method according to claim 1, wherein reaction (b) is performed without purposeful in vitro plasmid replication.

31. The method according to claim 1, wherein reactions (b), (c), and (d) are performed without purposeful in vitro plasmid displacement loop formation and without purposeful in vitro plasmid theta structure formation, and without prior purposeful formation of either of said forms.

32. The method according to claim 1, wherein reactions (b), (c), and (d) are performed without purposeful in vitro synthesis of RNA using an enzyme with RNA polymerase activity and using plasmid as a the template for the polymerase, and without prior such in vitro synthesis.

33. The method according to claim 1, wherein the plasmid solution does not further comprise purposefully in vitro-synthesized open circular plasmid prior to reaction (b).

34. The method according to claim 1, wherein the plasmid solution obtained by processing of the host cells further comprises supercoiled plasmid and reactions (b), (c), and (d) are performed without prior purposeful in vitro conversion of the supercoiled plasmid to an undesired form; and wherein reactions (b) and (c) are performed without prior purposeful in vitro conversion of the open circular plasmid to an undesired form.

35. The method according to claim 1, wherein the plasmid solution obtained by processing of the host cells further comprises supercoiled plasmid and reactions (b) and (c) are performed without prior purposeful separation of open circular plasmid from supercoiled plasmid.

36. The method according to claim 1, wherein the host cells contain supercoiled and wherein the plasmid solution is obtained by a process which does not separate greater than 10% of open circular plasmid from supercoiled plasmid.

37. The method according to claim 1, which does not further comprise an additional in vitro enzymatic reaction prior to completing reaction (d) which increases the amount of plasmid derived DNA greater than 5%.

38. The method according to claim 1, wherein reactions (b), (c), and (d) are performed so that the total amount of plasmid is substantially unchanged.

39. The method according to claim 1, wherein the percentage of plasmid which is supercoiled plasmid after reaction (d) is increased from the percentage of plasmid which is supercoiled plasmid in the plasmid solution immediately prior to reaction (b).

40. The method according to claim 1, wherein at least 90% of the total plasmid in the plasmid solution is in negatively supercoiled form after reaction (d).

41. The method according to claim 1 further comprising recovering the supercoiled plasmid after reaction (d).

42. The method according to claim 41, wherein the supercoiled plasmid recovery comprises purification of the supercoiled plasmid from the reaction (d).

43. The method according to claim 41, wherein the supercoiled plasmid recovery comprises chromatographic purification of the supercoiled plamid.

44. The method according to claim 41 further comprising transforming the recovered supercoiled plasmid into recipient cells.

45. The method according to claim 1, wherein reaction (b) is performed with a purified DNA polymerase, reaction (c) is performed with a purified DNA ligase, and reaction (d) is performed with a purified DNA gyrase.

46. The method of claim 1, wherein at least one of the enzymes used in reactions (b) or (c) is a purified form of the enzyme.

* * * * *